US007998506B2

(12) United States Patent
Bova

(10) Patent No.: US 7,998,506 B2
(45) Date of Patent: *Aug. 16, 2011

(54) NICOTINIC ACID COMPOSITIONS FOR TREATING HYPERLIPIDEMIA AND RELATED METHODS THEREFOR

(75) Inventor: David J Bova, Boca Raton, FL (US)

(73) Assignee: KOS Life Sciences, Inc., Weston, FL (US)

( * ) Notice: Subject to any disclaimer, the term of this patent is extended or adjusted under 35 U.S.C. 154(b) by 91 days.

This patent is subject to a terminal disclaimer.

(21) Appl. No.: 10/444,145

(22) Filed: May 23, 2003

(65) Prior Publication Data

US 2005/0118257 A1    Jun. 2, 2005

Related U.S. Application Data

(63) Continuation of application No. 09/478,325, filed on Jan. 6, 2000, now abandoned, which is a continuation of application No. 08/814,974, filed on Mar. 6, 1997, now Pat. No. 6,129,930, which is a continuation-in-part of application No. 08/368,378, filed on Jan. 14, 1995, now Pat. No. 6,080,428, which is a continuation-in-part of application No. 08/124,392, filed on Sep. 20, 1993, now abandoned.

(51) Int. Cl.
- *A61K 9/22* (2006.01)
- *A61K 9/20* (2006.01)
- *A61K 9/26* (2006.01)
- *A61K 9/52* (2006.01)
- *A61K 31/455* (2006.01)
- *A61K 47/00* (2006.01)

(52) U.S. Cl. ........ 424/468; 424/457; 424/464; 424/469; 424/470; 514/356; 514/781

(58) Field of Classification Search .................... 424/468
See application file for complete search history.

(56) References Cited

U.S. PATENT DOCUMENTS

| | | | |
|---|---|---|---|
| 2,510,164 A | 6/1950 | Woodward et al. |
| 2,540,979 A | 2/1951 | Clymer et al. |
| 2,749,274 A | 6/1956 | Buckwalter |
| 2,798,837 A | 7/1957 | Sahyun |
| 2,798,838 A | 7/1957 | Robinson |
| 2,805,977 A | 9/1957 | Robinson |
| 2,851,453 A | 9/1958 | Kennon et al. |
| 2,857,313 A | 10/1958 | Cooper et al. |
| 2,887,436 A | 5/1959 | Klioze et al. |
| 2,957,804 A | 10/1960 | Schuyler |
| 3,062,720 A | 11/1962 | Costello |
| 3,065,143 A | 11/1962 | Christenson et al. |
| 3,108,046 A | 10/1963 | Harbit |
| 3,116,204 A | 12/1963 | Siegel et al. |
| 3,134,719 A | 5/1964 | Sheth et al. |
| 3,143,469 A | 8/1964 | Debay et al. |
| 3,147,187 A | 9/1964 | Playfair |
| 3,193,461 A | 7/1965 | Elsen |
| 3,210,413 A | 10/1965 | Blank et al. |
| 3,272,832 A | 9/1966 | Nakano et al. |
| 3,336,200 A | 8/1967 | Krause et al. |
| 3,424,842 A | 1/1969 | Nurnberg |
| 3,495,011 A | 2/1970 | Fossel |
| 3,590,117 A | 6/1971 | Christenson et al. |
| 3,626,071 A | 12/1971 | Kariya et al. |
| 3,629,393 A | 12/1971 | Nakamota et al. |
| 3,629,453 A | 12/1971 | Waring |
| 3,634,584 A | 1/1972 | Poole |
| 3,639,636 A | 2/1972 | Barnhart |
| 3,709,991 A | 1/1973 | Miller |
| 3,721,735 A | 3/1973 | Thiffault |
| 3,773,920 A | 11/1973 | Nakamoto et al. |
| 3,795,691 A | 3/1974 | Douglas et al. |
| 3,806,601 A | 4/1974 | Mikite et al. |
| 3,849,554 A | 11/1974 | Winitiz |
| 3,859,437 A | 1/1975 | Weigand |
| 3,862,332 A | 1/1975 | Barnhart et al. |
| 3,868,416 A | 2/1975 | Albright et al. |
| 3,870,790 A | 3/1975 | Lowey et al. |
| 3,923,972 A | 12/1975 | Fields et al. |
| 3,924,001 A | 12/1975 | Albright et al. |

(Continued)

FOREIGN PATENT DOCUMENTS

EP    0109320 A1    5/1984

(Continued)

OTHER PUBLICATIONS

DiPalma JR, Thayer WS, "Use of Niacin as a Drug, Annual Review of Nutrition," vol. 11, pp. 169-187 (Jul. 1991).*
Schlierf G, Hess G, "Inhibition of Carbohydrate-Induced Hypertriglyceridemia by Nicotinic Acid," Artery, vol. 3, No. 2, pp. 174-179 (1977).*
Schlierf G, Dorow, E, "Diurnal Patterns of Triglycerides, Free Fatty Acids, Blood Sugar, and Insulin during Carbohydrate-Induction in Man and Their Modification by Nocturnal Suppression of Lipolysis," Journal of Clinical Investigation, vol. 52, pp. 732-740 (Mar. 1973).*
Grundy SM, Mok HY, Zech L, Berman M, "Influence of Nicotinic Acid on Metabolism of Cholesterol and Triglycerides in Man," Journal of Lipid Research, vol. 22, pp. 24-36 (1981).*
Kruse W, Raetzer H, Heuck CC, Oster P, Schellenberg B, Schlierf G, "Nocturnal Inhibition of Lipolysis in Man by Nicotinic Acid and Derivatives," European Journal of Clinical Pharmacology, vol. 16, pp. 11-15 (1979).*

(Continued)

*Primary Examiner* — John Pak
*Assistant Examiner* — Nathan W Schlientz
(74) *Attorney, Agent, or Firm* — Lisa V. Mueller; Polsinelli Shughart PC

(57) ABSTRACT

An orally administered antihyperlipidemia composition according to the present invention includes from about 250 to about 3000 parts by weight of nicotinic acid, and from about 5 to about 50 parts by weight of hydroxypropyl methylcellulose. Also, a method of treating hyperlipidemia in a hyperlipidemic having a substantially periodic physiological loss of consciousness, includes the steps of forming a composition having an effective antihyperlipidemic amount of nicotinic acid and a time release sustaining amount of a swelling agent. The method also includes the step of orally administering the composition to the hyperlipidemic once per day "nocturnally," that is in the evening or at night.

4 Claims, No Drawings

U.S. PATENT DOCUMENTS

| | | |
|---|---|---|
| 3,930,017 A | 12/1975 | Kummer et al. |
| 3,951,821 A | 4/1976 | Davidson |
| 3,957,976 A | 5/1976 | Sugimoto |
| 3,959,492 A | 5/1976 | Coulston |
| 3,965,255 A | 6/1976 | Bloch et al. |
| 3,977,404 A | 8/1976 | Theeuwes |
| 3,987,160 A | 10/1976 | Broughton et al. |
| 3,992,536 A | 11/1976 | Kleemann |
| 4,002,641 A | 1/1977 | Moller et al. |
| 4,008,719 A | 2/1977 | Theeuwes |
| 4,014,334 A | 3/1977 | Theeuwes et al. |
| 4,014,987 A | 3/1977 | Heller et al. |
| 4,034,087 A | 7/1977 | Voorhees |
| 4,034,758 A | 7/1977 | Theeuwes |
| 4,058,122 A | 11/1977 | Theeuwes et al. |
| 4,067,876 A | 1/1978 | Ferruti et al. |
| 4,077,407 A | 3/1978 | Theeuwes et al. |
| RE29,652 E | 5/1978 | Fields et al. |
| 4,088,778 A * | 5/1978 | Igarashi et al. ............... 514/458 |
| 4,102,806 A | 7/1978 | Kondo et al. |
| 4,115,550 A | 9/1978 | Fields et al. |
| 4,116,241 A | 9/1978 | Theeuwes et al. |
| 4,117,111 A | 9/1978 | Fields et al. |
| 4,126,672 A | 11/1978 | Sheth et al. |
| 4,140,755 A | 2/1979 | Sheth et al. |
| 4,160,020 A | 7/1979 | Ayer et al. |
| 4,160,452 A | 7/1979 | Theeuwes |
| 4,166,902 A | 9/1979 | Ferruti et al. |
| 4,167,558 A | 9/1979 | Sheth et al. |
| 4,169,944 A | 10/1979 | Scallen et al. |
| 4,178,387 A | 12/1979 | Diamond et al. |
| 4,180,064 A | 12/1979 | Heller et al. |
| 4,182,902 A | 1/1980 | Thiele et al. |
| 4,203,439 A | 5/1980 | Theeuwes |
| 4,205,085 A | 5/1980 | Shepherd |
| 4,211,783 A | 7/1980 | Shepherd |
| 4,226,849 A | 10/1980 | Schor |
| 4,230,878 A | 10/1980 | Shepherd |
| 4,237,118 A | 12/1980 | Howard |
| 4,248,857 A | 2/1981 | DeNeale et al. |
| 4,251,519 A | 2/1981 | Robbins et al. |
| 4,255,449 A | 3/1981 | Cavazza |
| 4,256,108 A | 3/1981 | Theeuwes |
| 4,259,314 A | 3/1981 | Lowey |
| 4,259,332 A * | 3/1981 | Passoni et al. ................ 514/166 |
| 4,261,970 A | 4/1981 | Ogawa et al. |
| 4,268,524 A | 5/1981 | Cavazza |
| 4,272,548 A | 6/1981 | Gatzen et al. |
| 4,279,898 A | 7/1981 | Engel et al. |
| 4,282,233 A | 8/1981 | Vilani |
| 4,283,382 A | 8/1981 | Frank et al. |
| 4,285,951 A | 8/1981 | Hoefle |
| 4,291,030 A | 9/1981 | Mulinos |
| 4,305,959 A | 12/1981 | Shepherd |
| 4,308,251 A | 12/1981 | Dunn et al. |
| 4,309,404 A | 1/1982 | DeNeale et al. |
| 4,310,545 A | 1/1982 | Shepherd |
| 4,318,914 A | 3/1982 | Shepherd |
| 4,326,525 A | 4/1982 | Swanson et al. |
| 4,348,399 A | 9/1982 | Shepherd |
| 4,353,887 A | 10/1982 | Hess et al. |
| 4,357,469 A | 11/1982 | Schor |
| 4,361,546 A | 11/1982 | Stricker et al. |
| 4,362,711 A | 12/1982 | Cerami |
| 4,367,217 A | 1/1983 | Gruber et al. |
| 4,369,172 A | 1/1983 | Schor et al. |
| 4,375,468 A | 3/1983 | Dunn |
| 4,382,143 A | 5/1983 | Shepherd |
| 4,389,393 A | 6/1983 | Schor et al. |
| 4,428,951 A | 1/1984 | Hata et al. |
| 4,432,966 A | 2/1984 | Zeitoun et al. |
| 4,440,940 A | 4/1984 | Shepherd |
| 4,452,775 A | 6/1984 | Kent |
| 4,454,108 A | 6/1984 | Iida et al. |
| 4,455,298 A | 6/1984 | McFarlane et al. |
| 4,457,907 A | 7/1984 | Porter |
| 4,461,759 A | 7/1984 | Dunn |
| 4,465,660 A | 8/1984 | David et al. |
| 4,472,436 A | 9/1984 | Hooper |
| 4,478,819 A | 10/1984 | Hercelin et al. |
| 4,485,105 A | 11/1984 | Shepherd |
| 4,505,890 A | 3/1985 | Jain |
| 4,522,804 A | 6/1985 | Dunn |
| 4,525,345 A | 6/1985 | Dunn et al. |
| 4,539,198 A | 9/1985 | Powell et al. |
| 4,540,566 A | 9/1985 | Davis et al. |
| 4,547,359 A | 10/1985 | Zierenberg et al. |
| 4,556,678 A | 12/1985 | Hsiao |
| 4,568,547 A | 2/1986 | Herschler |
| 4,571,333 A | 2/1986 | Hsiao et al. |
| 4,576,604 A | 3/1986 | Guittard et al. |
| 4,603,142 A | 7/1986 | Burger et al. |
| 4,605,666 A | 8/1986 | Schmidt et al. |
| 4,610,870 A | 9/1986 | Jain et al. |
| 4,624,950 A | 11/1986 | Sasaki et al. |
| 4,657,757 A | 4/1987 | Hanna et al. |
| 4,661,353 A | 4/1987 | Wilton et al. |
| 4,673,405 A | 6/1987 | Guittard et al. |
| 4,678,516 A | 7/1987 | Alderman et al. |
| 4,680,323 A | 7/1987 | Lowey |
| 4,684,516 A | 8/1987 | Bhutani |
| 4,690,824 A | 9/1987 | Powell et al. |
| 4,692,337 A | 9/1987 | Ukigaya et al. |
| 4,695,467 A | 9/1987 | Uemura et al. |
| 4,695,591 A | 9/1987 | Hanna et al. |
| 4,695,910 A | 9/1987 | Maruyama et al. |
| 4,696,762 A | 9/1987 | Sander et al. |
| 4,704,285 A | 11/1987 | Alderman |
| 4,708,834 A | 11/1987 | Cohen et al. |
| 4,710,519 A | 12/1987 | Finnan et al. |
| 4,713,245 A | 12/1987 | Ando et al. |
| RE32,581 E | 1/1988 | Scherm et al. |
| 4,734,285 A | 3/1988 | Alderman |
| 4,747,881 A | 5/1988 | Shaw et al. |
| 4,749,575 A | 6/1988 | Rotman |
| 4,752,479 A | 6/1988 | Briggs et al. |
| 4,753,801 A | 6/1988 | Oren et al. |
| 4,755,544 A | 7/1988 | Makino et al. |
| 4,756,911 A | 7/1988 | Drost et al. |
| 4,758,581 A | 7/1988 | Scherm et al. |
| 4,759,923 A | 7/1988 | Buntin et al. |
| 4,764,374 A | 8/1988 | Grimberg |
| 4,775,483 A | 10/1988 | Mookerjea et al. |
| 4,775,535 A | 10/1988 | Lowey |
| 4,777,042 A | 10/1988 | Toda et al. |
| 4,784,858 A | 11/1988 | Ventouras |
| 4,789,549 A | 12/1988 | Khan et al. |
| 4,792,452 A | 12/1988 | Howard et al. |
| 4,792,554 A | 12/1988 | Elben et al. |
| 4,794,115 A | 12/1988 | Takahashi et al. |
| 4,795,327 A | 1/1989 | Gaylord et al. |
| 4,795,642 A | 1/1989 | Cohen et al. |
| 4,795,644 A | 1/1989 | Zentner |
| 4,803,079 A | 2/1989 | Hsiao et al. |
| 4,803,081 A | 2/1989 | Falk et al. |
| 4,812,316 A | 3/1989 | Rossi et al. |
| 4,814,183 A | 3/1989 | Zentner |
| 4,814,354 A | 3/1989 | Ghebre-Sellassie et al. |
| 4,824,672 A | 4/1989 | Day et al. |
| 4,824,677 A | 4/1989 | Shah et al. |
| 4,828,836 A | 5/1989 | Elger et al. |
| 4,829,895 A | 5/1989 | Juhuku |
| 4,830,859 A | 5/1989 | Finnan et al. |
| 4,834,965 A | 5/1989 | Martani et al. |
| 4,834,985 A | 5/1989 | Elger et al. |
| 4,837,032 A | 6/1989 | Ortega |
| 4,839,177 A | 6/1989 | Colombo et al. |
| 4,842,863 A | 6/1989 | Nishimura et al. |
| 4,844,907 A | 7/1989 | Elger et al. |
| 4,849,229 A | 7/1989 | Gaylord et al. |
| 4,851,232 A | 7/1989 | Urquhart et al. |
| 4,851,233 A | 7/1989 | Khan et al. |
| 4,855,143 A | 8/1989 | Lowery |
| 4,857,336 A | 8/1989 | Khanna et al. |
| 4,866,058 A | 9/1989 | Izydore et al. |
| 4,871,548 A | 10/1989 | Edgren et al. |
| 4,882,167 A | 11/1989 | Jang |

| | | |
|---|---|---|
| 4,886,669 A | 12/1989 | Ventouras |
| 4,888,178 A | 12/1989 | Rotini et al. |
| 4,892,741 A | 1/1990 | Ohm et al. |
| 4,911,917 A | 3/1990 | Kuhrts |
| 4,915,952 A | 4/1990 | Ayer et al. |
| 4,920,115 A | 4/1990 | Nestler et al. |
| 4,920,123 A | 4/1990 | Beyer, Jr. |
| 4,925,905 A | 5/1990 | Boeckh et al. |
| 4,935,246 A | 6/1990 | Ahrens |
| 4,940,588 A | 7/1990 | Sparks et al. |
| 4,942,040 A | 7/1990 | Ragnarsson et al. |
| 4,946,870 A | 8/1990 | Partain, III. et al. |
| 4,946,963 A | 8/1990 | Izydore et al. |
| 4,950,689 A | 8/1990 | Yang et al. |
| 4,952,402 A | 8/1990 | Sparks et al. |
| 4,959,478 A | 9/1990 | Moller et al. |
| 4,963,367 A | 10/1990 | Ecanow |
| 4,965,252 A | 10/1990 | Kuhrts |
| 4,966,768 A | 10/1990 | Michelucci et al. |
| 4,968,508 A | 11/1990 | Oren et al. |
| 4,970,081 A | 11/1990 | Frisbee |
| 4,970,221 A | 11/1990 | Magnin et al. |
| 4,973,468 A | 11/1990 | Chiang et al. |
| 4,973,469 A | 11/1990 | Mulligan et al. |
| 4,983,398 A | 1/1991 | Gaylord et al. |
| 4,990,535 A | 2/1991 | Cho et al. |
| 4,992,278 A | 2/1991 | Khanna |
| 4,994,267 A | 2/1991 | Sablotsky |
| 4,994,276 A | 2/1991 | Baichwal et al. |
| 4,996,058 A | 2/1991 | Sinnreich |
| 4,997,658 A | 3/1991 | Alberts et al. |
| 4,999,380 A | 3/1991 | Berger et al. |
| 5,002,774 A | 3/1991 | Agrawala |
| 5,009,895 A | 4/1991 | Lui |
| 5,010,105 A | 4/1991 | Lee |
| 5,011,947 A | 4/1991 | Catt et al. |
| 5,015,479 A | 5/1991 | Mulligan et al. |
| 5,022,774 A | 6/1991 | Kageyama et al. |
| 5,023,245 A * | 6/1991 | Kuhrts ............................. 514/54 |
| 5,025,012 A | 6/1991 | Miura et al. |
| 5,030,653 A | 7/1991 | Trivedi |
| 5,032,406 A | 7/1991 | Dansereau et al. |
| 5,032,608 A | 7/1991 | Dudrick |
| 5,034,528 A | 7/1991 | Izydore et al. |
| 5,039,341 A | 8/1991 | Meyer |
| 5,047,248 A | 9/1991 | Calanchi et al. |
| 5,049,696 A | 9/1991 | Lee et al. |
| 5,096,714 A | 3/1992 | Kuhrts |
| 5,100,675 A | 3/1992 | Cho et al. |
| 5,110,817 A | 5/1992 | Beyer, Jr. |
| 5,110,940 A | 5/1992 | Sit et al. |
| 5,116,610 A | 5/1992 | Broaddus |
| 5,126,145 A * | 6/1992 | Evenstad et al. ............. 424/465 |
| 5,126,348 A * | 6/1992 | McMurray ............... 514/263.32 |
| 5,128,142 A | 7/1992 | Mulligan et al. |
| 5,130,333 A | 7/1992 | Pan et al. |
| 5,132,116 A | 7/1992 | Sournac et al. |
| 5,133,974 A | 7/1992 | Paradissis et al. |
| 5,145,678 A | 9/1992 | Gakic et al. |
| 5,167,964 A | 12/1992 | Muhammad et al. |
| 5,169,638 A | 12/1992 | Dennis et al. |
| 5,169,639 A | 12/1992 | Baichwal et al. |
| 5,169,640 A | 12/1992 | France et al. |
| 5,171,570 A | 12/1992 | Takemori et al. |
| 5,178,854 A | 1/1993 | Asami et al. |
| 5,182,298 A | 1/1993 | Helms et al. |
| 5,188,839 A | 2/1993 | Pearmain |
| 5,190,940 A | 3/1993 | Commons et al. |
| 5,190,970 A | 3/1993 | Pan et al. |
| 5,196,440 A | 3/1993 | Bertolini et al. |
| 5,211,958 A | 5/1993 | Akkerboom et al. |
| 5,213,808 A | 5/1993 | Bar-Shalom et al. |
| 5,256,689 A | 10/1993 | Chiang |
| 5,258,401 A | 11/1993 | Berger et al. |
| 5,260,305 A | 11/1993 | Dennick |
| 5,262,165 A | 11/1993 | Govil et al. |
| 5,262,435 A | 11/1993 | Joshua et al. |
| 5,264,226 A | 11/1993 | Graille et al. |
| 5,268,181 A * | 12/1993 | O'Neill et al. .................. 424/465 |
| 5,278,067 A | 1/1994 | Dawson et al. |
| 5,286,736 A | 2/1994 | Soyka et al. |
| 5,314,697 A | 5/1994 | Kwan et al. |
| 5,773,453 A | 6/1998 | Roberts, II et al. |
| 5,981,555 A | 11/1999 | Kuhrts et al. |
| 6,080,428 A * | 6/2000 | Bova ............................ 424/468 |
| 6,129,930 A * | 10/2000 | Bova ............................ 424/468 |
| 6,406,715 B1 | 6/2002 | Cefali |
| 6,469,035 B1 | 10/2002 | Cefali |
| 6,676,967 B1 | 1/2004 | Cefali et al. |
| 6,746,691 B2 | 6/2004 | Cefali |
| 6,818,229 B1 | 11/2004 | Cefali |
| 7,011,848 B1 * | 3/2006 | Bova ............................ 424/468 |
| 2003/0157153 A1 | 8/2003 | Cefali |
| 2006/0171970 A1 | 8/2006 | Karl |
| 2006/0263428 A1 | 11/2006 | Cefali |
| 2007/0225341 A1 | 9/2007 | Cefali |
| 2007/0232667 A1 | 10/2007 | Cefali |
| 2007/0237819 A1 | 10/2007 | Bova |
| 2008/0045573 A1 | 2/2008 | Bova |
| 2008/0050429 A1 | 2/2008 | Rocca et al. |
| 2008/0300284 A1 | 12/2008 | Bova |
| 2009/0036500 A1 | 2/2009 | Bova |
| 2010/0076033 A1 | 3/2010 | Cefali |

FOREIGN PATENT DOCUMENTS

| | | |
|---|---|---|
| EP | 0126453 A2 | 11/1984 |
| EP | 0349 235 A2 | 1/1990 |
| EP | 0577 504 A1 | 1/1994 |
| EP | 643965 | 3/1995 |
| EP | 0643965 A1 | 3/1995 |
| WO | WO 84/00104 | 1/1984 |
| WO | WO9632942 | 10/1996 |
| WO | WO 99/06035 | 2/1999 |
| WO | WO 00/33818 | 6/2000 |
| WO | WO 2006/089309 | 8/2006 |
| WO | WO2006/102476 | 9/2006 |

OTHER PUBLICATIONS

Carlson LA, Hamsten A, Asplund A, "Pronounced Lowering of Serum Levels of Lipoprotein Lp(a) in Hyperlipidemic Subjects Treated with Nicotinic Acid," Journal of Internal Medicine, vol. 226, pp. 271-276 (1989).*

Keenan JM, Fontaine PL, Wenz JB, Myers S, Huang ZQ, Ripsin CM, "Niacin revisited. A randomized, controlled trial of wax-matrix sustained-release niacin in hypercholesterolemia," Arch Intern Med, vol. 151, No. 7, pp. 1424-1432 (Jul. 1991).*

Keenan JM, Wenz JB, Ripsin CM, Huang ZQ, McCaffrey DJ, "A clinical trial of oat bran and niacin in the treatment of hyperlipidemia," Journal of Family Practice, vol. 34, No. 3, pp. 313-319 (Mar. 1992).*

Lavie CJ, Mailander L, Milani RV, "Marked Benefit with Sustained-Release Niacin Therapy in Patients with 'Isolated' Very Low Levels of High-Density Lipoprotein Cholesterol and Coronary Artery Disease," Am J of Cardiology, vol. 69, pp. 1083-1085 (1992).*

Yin Ruixing, Chen Yuming, Pan Shangling, He Fengping, Liu Tangwei, Yang Dezhai, Wu Jinzhen, Yao Limei, Lin Weixiong, Li Rongshan, and Huang Jiandong, "Comparison of Lipid Levels, Hyperlipidemia Prevalence and Its Risk Factors between Guangxi Hei Yi Zhuang and Han Populations", Archives of Medical Research, 2006, vol. 37, pp. 787-793.*

Expert Report of Cheryl D. Blume, Ph.D. (Jan. 27, 2004)—Subject to Protective Order-.

Expert Report of Dr. Sergio Fazio (Feb. 4, 2004) [Redacted Version]—Subject to Protective Order-.

Rebuttal Expert Report of Dr. Sergio Fazio (Apr. 2, 2004)—Subject to Protective Order-.

Expert Report of Dr. Sergio Fazio Regarding U.S. Patent No. 6,676,967 (Aug. 17, 2004)—Subject to Protective Order-.

Expert Report of Don W. Martens (Feb. 6, 2004) [Redacted Version]—Subject to Protective Order-.

Expert Report of Don W. Martens Regarding U.S. Patent No. 6,676,967 (Aug. 20, 2004) [Redacted Version]—Subject to Protective Order-.

Expert Report of Dr. Joseph R Robinson (Feb. 5, 2004) [Redacted Version]—Subject to Protective Order-.

Expert Report of Dr. Joseph R. Robinson Regarding US. Patent No. 6,676,967 (Aug. 18, 2004)—Subject to Protective Order-.
Rebuttal Expert Report of Thomas S. Foster, Pharm.D. (Apr. 2, 2004)—Subject to Protective Order-.
Rebuttal Expert Report of Thomas S. Foster, Pharm.D. Regarding The '967 Patent (Oct. 4, 2004)—Subject to Protective Order-.
Rebuttal Expert Report of James W. McGinity, Ph.D. (Apr. 2, 2004)—Subject to Protective Order-.
Supplemental Rebuttal Expert Report of James W. McGinity, Ph.D. (Aug. 18, 2004)—Subject to Protective Order-.
Rebuttal Expert Report of James W. McGinity, Ph.D. Regarding The '967 Patent (Sep. 30, 2004)—Subject to Protective Order-.
Expert Report of Mark E. McGovern, M.D. (Feb. 6, 2004)—Subject to Protective Order-.
Expert Report of Mark E. McGovern, M.D. (Aug. 20, 2004)—Subject to Protective Order-.
Expert Report of Frank M. Sacks, M.D. (Apr. 2, 2004)—Subject to Protective Order-.
Expert Report of Frank M. Sacks, M.D. (Aug. 20, 2004)—Subject to Protective Order-.
Rebuttal Expert Report of Mary Ann Tucker, Esq. (Apr. 2, 2004)—Subject to Protective Order-.
Rebuttal Expert Report of Mary Ann Tucker, Esq. Regarding The '967 Patent (Oct. 1, 2004)—Subject to Protective Order-.
Sample Kos Clinical Trial Medical Consent Form—Subject to Protective Order-.
Sample Kos Clinical Trial Investigator's Statement—Subject to Protective Order-.
Lavie, et al., Marked Benefit with Sustained-Release Niacin Therapy in Patients with "isolated" Very Low Levels of High-Density Lipoprotein Cholesterol and Coronary Artery Disease, *Am. J. Cardiol.*; 69:1083-1085 (1992).
Physician's Desk Reference, Excerpts (1993, 2000, and 2002): 1993 edition (pp. 434, 611, 856, 1189, 1919, 1920, 2491, and 2492); 2000 edition (pp. 1519-1523); 2002 edition (pp. 1846-1850).
Niacin: Double-edged Sword for Lowering Cholesterol, *Tufts University Diet & Nutritional Letter* (Tufts Univ., Boston, MA), 12(6) (1994).
Larsen, et al., Drug Treatment of Dyslipoproteinemia, *Med. Clin. N. Am.*; 78:225-245 (1994).
Lavie, Letter to Editor, *JAMA*; 272:513-515 (1994).
Keenan, Letter to Editor, *JAMA*; 272:513-515 (1994).
Shields & Beckmann, Letter to Editor, *JAMA*; 272:513-515 (1994).
Tozer, Clinical Pharmacokinetics Concepts and Applications; Chapter 9, p. 120 (3d ed. 1995).
United States Pharmacopeia Excerpts, pp. iii-vi, 1080-1082, 1793-1799, and 1940-1944 (1995).
Morgan & Capuzzi, (abstract) Safe and Effective Treatment of Dyslipidemia by Niaspan, a New Sustained-Release Niacin, *Clinical Pharmacology & Therapeutics*; (Feb. 1996).
Morgan & Capuzzi, Treatment Effect of Niaspan, a Controlled-released Niacin, inPatients With Hypercholesterolemia: A Placebo-controlled Trial, *J. Cardiovasc. Pharmacol. Therapeut.*; 1(3):195-2002 (Jul. 1996).
Capuzzi, et al., Efficacy and Safety of An Extended-Release Niacin (Niaspan): A Long-Term Study, *Am. J. Cardiol.*; 82:74U-81U (1998).
Guyton, Advances in Dyslipidemia: Discussion Session II, *Am. J. Cardiol.*; 82(12A):85U-86U (1998).
Knopp, et al., Equivalent Efficacy of a Time-Release Form of Niacin (Niaspan) Given Once-a-Night Versus Plain Niacin in the Management of Hyperlipidemia, *Metabolism*; 47:1097-1104 (1998).
American Diabetes Association: Management of Dyslipidemia in Adults with Diabetes, *Diabetes Care*; 21:179-182 (1998).
Elam, et al., Effect of Niacin on Lipid and Lipoprotein Levels and Glycemic Control in Patients With Diabetes and Peripheral Arterial Disease, *JAMA*; 284:1263-1270 (2000).
Kesala, et al., Niacin (N) vs. Niaspan (NS) Treatment of the Atherogenic Lipid Profile (ALP; Small, Dense LDL, HDL2, HDLc and Triglycerides) and Lp(a) in Diabetic Patients (DP), *Diabetes*; 49 (suppl. I): A268 at 1114-P (Jun. 2000).
NCEP Report at VI-11, Table VI.2-3 (2001).

Wang, et al., Effect of Nicotinic Acid Administration on Hepatic Very Low Density Lipoprotein-Triglyceride Production, Am. J. Physiol. *Endocrinol. Metab.*; 280:E540-E547 (2001).
Smith, et al., AHA/ACC Guidelines for Preventing Heart Attack and Death in Patients with Atherosclerotic Cardiovascular Disease: *AHA/ACC Scientific Statement*; 1577-1579 (2001 Update).
Tavintharan, et al., The Benefits of Niacin in Atherosclerosis, *Curr. Athero. Reports*; 3:74-82 (2001).
Meadows, Serious Liver Injury: Leading Reason for Drug Removals, Restrictions, *FDA Consumer Magazine*; available at: http://www.fda.govlfdac/features12001/301~liver.html (May-Jun. 2001).
Grundy, et al., Efficacy, Safety, and Tolerability of Once-Daily Niacin for the Treatment of Dyslipidemia Associated with Type 2 Diabetes, *Arch. Intern. Med.*; 162:1568-1576 (2002).
American Diabetes Association: Management of Dyslipidemia in Adults with Diabetes, *Diabetes Care*; 25:S74-S77 (2002).
Pan, et al., Niacin Treatment of the Atherogenic Lipid Profile and Lp(a) in Diabetes, Diabetes, *Obesity and Metabolism*; 4:255-261 (2002).
Pan, et al., Extended-Release Niacin Treatment of the Atherogenic Lipid Profile and Lipoprotein(a) in *Diabetes, Metabolism*; 51:1120-1127 (2002).
Meyers, et al., Varying Cost and Free Nicotinic Acid Content in Over-the-Counter Niacin Preparations for Dyslipidemia, *Ann. Intern. Med.*; 139:996-1002 (2003).
CDER Guidance for Industry, Bioavailability and Bioequivalence Studies for Orally Administered Drug Products—General Considerations (Mar. 2003).
American Diabetes Association: Dyslipidemia Management in Adults with Diabetes, *Diabetes Care*; 27:S68-S71 (2004).
Luria, M., Arch., Intern. Med., 148:2493-2495 (Nov. 1988).
"Niaplus Product Information" from the Physician's Desk Reference (1988).
Remington's Pharmaceutical Sciences, pp. 1636-1637, 1990.
Urberg M et al: Metabolism, 36(9):896-899 (Sep. 1987).
Blankenhorn D H et al: JAMA, 257(23):159-166 (Jun. 19, 1987).
Canner P L et al: JACC, 8(6):1245-1255 (Dec. 1986).
Sokoloski T D: Solutions and Phase Equilibria, in Remington's 17th Edition Pharmaceutical Sciences, Mack Publishing Company, 207-208 (1985).
Knopp R H et al: Metabolism, 34(7):642-650 (Jul. 1985).
Korsmeyer R W et al: Journal of Pharmaceutical Sciences, 72(10):1189,1191 Oct. 1983.
Dow Chemical Company publication, 1-15 (1985).
The Merck Index, Merck & Co. Inc., Tenth Edition, 809,520,351,466 (1983).
Malkowska S et al: Drug Development and Industrial Pharmacy, Marcel Dekker, Inc., 9(3):349-361 (1983).
Blum C B et al: JAMA, 261(24):3582-3587 (1989).
1989 Dow Chemical Company publication which appears to relate to formulating for controlled release with Methocel premium cellulose ethers.
Kowalski R.E.: The 8-Week Cholesterol Cure, Harper & Row, Publishers, 95-115 and notes 345-346 (1989).
Manninen M et al: JAMA, 260(5):641-651 (1988).
Figge H L et al: J. Clin. Pharmacol., 28:1136-1140 (1988).
Figge H L et al: Pharmacotherapy, 8(5):287-294 (1988).
Urberg M et al: The Journal of Family Practice, 27(6):603-606 (1988).
Wahlberg G et al: Acta. Med. Scand., 224:319-327 (1988).
Chain Drug Review Publication, p. 12, Jun. 6, 1988, P. Leiner.
Cooper K H: Bantam Books, Dr. Kenneth H. Cooper's Preventive Medicine Program, Controlling Cholesterol, 244-253 (1988).
Laguna O et al: Annales Pharmaceutiques Francaises, 33(5):235-242 (1975).
Fleischman A I et al: Fed. Proc. 34(1), 248 (1975).
Remington's Pharmaceutical Sciences, 1576-1587 (1975).
Remington's Pharmaceutical Sciences, 1242-1251 (1975).
Schlierf G et al: Nutr. Metabol., 13:80-91 (1971).
Barter P J et al: The Journal of Clinical Investigation, 50:583-591 (1971).
Miettinen T A: Annals of Clinical Research, 2:300-320 (1970).
Ekstrom-Jodal B et al: Pharmacologia Clinica, 2:86-89 (1970).

Lapidus H et al: Journal of Pharmaceutical Sciences, 57(8):1292-1301 (Aug. 1968).
Carlson L A et al: Acta Med Scand, 183(5):457-465 (May 1968).
Rader J I et al: The American Journal of Medicine, 92:77-81 (Jan. 1992).
Etchason J A et al: Mayo Clin. Proc., 66:23-28 (1991).
Keenan J M: JAMA Specialty Journal Abstracts, 266(16):2209 (1991).
Henkin Y et al: JAMA, 264(2):241-243 (1990).
Handbook of Nonprescription Drugs, Nutritional Supplements, 9th Edition, American Pharmaceutical Association, 470-471 (1990).
Schulman K A et al: JAMA, 264(23):3025-3033 (Dec. 19, 1990).
Brown G et al: The New England Journal of Medicine, 323(19):1289-1298 (Nov. 8, 1990).
Alderman J D et al: Am. J. Cardiol., 64(12):725-729 (Oct. 1, 1989).
Alderman, JD et al: Clinical Research: Ischemic Heart Disease—Drug Therapy, Abstracts of the 58th Scientific Sessions, 1883, III-471 (1985).
Buriet P et al: Pharm. ACTA Helv., 33(7-8):189-197 (1980).
Davis S S et al: Modern Concepts in Nitrate Delivery Systems, 29-37, edited by A.A.J. Goldberg and D.G. Parsons, 1983: Royal Society of Medicine International Congress and Symposium Series No. 54, published jointly by Academic Press Inc. (London) Ltd., and the Royal Society of Medicine.
Salomon J L et al: Pharm. ACTA Helv., 54(3):82-85 (1979).
Ibrahim, S A et al: Pharmazie, 35(8):567 (1980).
Pintye-Hodi K et al: Pharmazier, 35(3):168-170 (1980).
Shepherd J et al: J. Clin. Invest, 63:858-867 (May 1979).
The Coronary Project Research Group: JAMA, 231(4):36-381 (Jan. 27, 1975).
Chowhan T et al: Journal of Pharmaceutical Sciences, 67(10):1385-1389 Oct. 1978).
Salomon J L et al: Pharm. ACTA Helv., 54(3):75-85 (1979).
Salomon J L et al: Pharm. Ind., 41(8):799-802 (1979).
Abumrad N A et al: Journal of Lipid Research, 19:423-432 (1978).
Japanese Patent Abstract, No. 0049312, which is dated Apr. 1980.
PCT Publication No. WO 84/00104, which was published on Jan. 19, 1984.
EPO Patent Abstract, No. 0109320, which is dated May 23, 1984.
EPO Patent Application No. 0126453, which is dated Nov. 28, 1984.
United Kingdom Patent Application No. 2 141 338 A, which was published on Dec. 19, 1984.
United Kingdom Patent Application No. 2 154 874 A, which was published on Sep. 18, 1985.
EPO Patent Publication No. 0 109320, which was published on Jun. 25, 1986.
Jacobson T A et al: The American Journal of Cardiology, 73:25D-29D (May 26, 1994).
Kane J P et al: The New England Journal of Medicine, 304(5):251-258 (Jan. 29, 1981).
Chowhan Z T et al: Journal of Pharmaceutical Sciences, 70(10):1134-1139 (Oct. 1981).
Cayen M N: Drug Metabolism Reviews, 11(2):291-323 (1980).
Rowland M et al: Clinical Pharmacokinetics: Concepts and Applications publication, Lea & Febiger, 111 (1980).
Chowhan Z T: Journal of Pharmaceutical Sciences, 69(1):1-3 (Jan. 1980).
Gudsoorkar, V R et al: Indian Drugs & Pharmaceuticals Industry, 3-4 (Jul.-Aug. 1980).
Krycer I et al: Powder Technology, 34:39-51 (1983).
1982 Dow Chemical Company publication is entitled "Technical Information: Methods of Formulating Controlled Release Products Outside the Forest Lab Patent U.S. 4,389,393 Claims."
1982 Dow Chemical Company publication is entitled "Formulating Sustained Release Pharmaceutical Products with Methocel."
1987 Dow Chemical Company publication is entitled "Formulating for Controlled Release with Methocel cellulose Ethers."
1988 Slow-Niacin Advertisement, American Druggist, 141-142 (Apr. 1988).
Hunninghake D B: Upsher-Smith Laboratories, Inc. publication 1990.
1988 Regulatory Letter addressed to Upsher-Smith Laboratories, and dated Jun. 1988.
1989 Dow Chemical Company publication is entitled "Formulating for Controlled Release with Methocel cellulose Ethers".
Canadian Patent No. 603,690, which issued on Aug. 16, 1960 to Hamada.
French Patent No. 1.302.362, which issued on Jul. 23, 1962.
Japanese Patent Abstract, No. 40/2053, which is dated Feb. 1965.
Japanese Patent Abstract No. 46-18151, which is dated May 1971.
Lapidus H: Chemistry, 2363-B-2364-B (1967).
Dow Chemical: Handbook on Methocel Cellulose Ether Products, 1960.
Svedmyr N: Clinical Pharmacology and Therapeutics, 559-570 (1960).
Alderman J D et al: Clinical Research, Abstract 1883, III-471 (Oct. 1985).
Carlson, L A: Annals New York Academy of Sciences, 119-142 (1985).
Dow Chemical: (1985) appears to relate to product designation changes for methocel cellulose ethers.
Kassem A A et al: Jami at Al-Qahira, Faculty of Pharmacy, Bulletin, Cairo, 19(1):275-306 (1980).
Lapidus H: Chemistry, Abstract, (order No. 67-14, 728) 2363-B-2364-B (1967).
Dow Chemical Company Publication: (1974) appears to relate to a handbook on methocel cellulose ether products.
Svedymr N et al: Clinical Pharmacology and Therapeutics, 10(4):559-570 (1974).
Reexamination Certificate No. B1 4,389,393 Published Oct. 22, 1985.
Mahl M: The American Journal of the Medical Sciences, 64:673-677 (Dec. 1963).
Carlson L A et al: Acta Medica Scandinavica, 172:641-645 (fasc. 6, 1962).
Carlson L A: Acta Medica Scandinavica, 173:719-722 (fasc. 6, 1963).
Berge K G et al: American Journal of Medicine, 31:24-35 (Jul. 1961).
Lapidus H et al: Journal of Pharmaceutical Sciences, 57(8):1292-1301 (Aug. 1968).
Christensen N A et al: J.A.M.A., 177(8):76-80 (Aug. 26, 1961).
Carlson L A et al: The Journal of Clinical Investigation, 47:1795-1805 (1968).
Altschul R et al: Academic Press Inc., 51:308-309 (1954).
Carlson L A: Progr. Biochem. Pharmacol., 3:151-166 (1967).
Miller O N et al: American Journal of Clinical Nutrition, 8:480-490 (Jul.-Aug. 1960).
Pinter E.J. et al: Preliminary Communications, 27:440-443 (Mar. 1967).
Lapidus H: University Microfilms International, Thesis, Rutgers University, 1-117, 1983.
Carlson L A: Annals New York Academy of Sciences, III(471):118-143 (1960).
Lapidus H et al: Journal of Pharmaceutical Sciences, 55(8):840-843 (Aug. 1966).
Dow Chemical: (1960) appears to relate to product designation changes for methocel cellulose ethers.
Kassem A A et al: Department of Pharmaceuticals, Faculty of Pharmacy, Cairo University, 275-306 (1960).
Huber H E et al: Journal of Pharmaceutical Sciences, 55:974-976 (Sep. 1966).
Carlson L A: Clinica Crimica Acta, 13:349-350 (1966).
Carlson L A et al: Acta Medica Scandinavica, 179:453-461 (Apr. 1966).
Altschul R et al: Charles C. Thomas, 42-135 (1964).
Letter, JAMA, 264(2):181 (Jul. 11, 1990).
Schlierf G et al: Artery, 3(2):174-179 (1977).
Schlierf G et al: J. Clin. Invest., 52(3):732-740 (Mar. 1973).
Abstract, Schlierf G et al: Pharmacological Control of Lipid Metabolism, Proceedings of the Fourth International Symposium on Drugs Affecting Lipid Metabolism, Philadelphia, PA, 26:319-320 (Sep. 1971).
Criscuoli M et al: Artherosclerosis, 53(1):59-68 (1984).
Renzetti A R et al: J. Pharm Pharmacol., 37(12):906-909 (Dec. 1985).
Miettinen T A: Annals of Clinical Research, 12:295-298 (1980).
Miettinen T A: Metabolism, 34(5):425-430 (May 1985).

Miettinen T A: J. Lipid Research, 23:466-473 (1982).
Regulatory Letter, Department of Health & Human Services, addressed to Nutritional Products, Inc. (Feb. 21, 1989).
Subissi A et al: J. Pharm. Pharmacol., 35(9):571-575 (Sep. 1983).
Kruse W et al: Eur. J. Clin. Pharmacol., 16:11-15 (1979).
Altschul R: Arch. Biochem. Bophys, 54:448-559 (1955).
Carlson L A et al: Acta Med. Scand., 183:457-465 (1968).
Neuvonen P J et al: Br. J. Clin. Pharmac., 32:473-476 (1991).
Keenan J M et al: JAGS, 40:12-18 (1992).
Cayen M N et al: Artherosclerosis, 45(3):281-290 (Dec. 1982).
Angleton et al., "Diurnal Variation of Tissue-Type Plasminogen Activator and Its Rapid Inhibitor (PAI-1)" from the Department of Laboratory Medicine, University of Washington, Sep. 1988 (1 page).
Chandler et al., "Insulin, Cortisol and Catecholamines Do Not Regulate Circadian Variations in Fibrinolytic Activity", Thrombosis Research, 58(1):1-12 (1990).
Dalton et al., "Hepatotoxicity Associated with Sustained-Release Niacin", the American Journal of Medicine, 93, 102-104 (Jul. 1992).
Hamsten et al., "Increased Plasma Levels of a Rapid Inhibitor of Tissue Plasminogen Activator in Young Survivors of Myocardial Infarction," The New England Journal of Medicine, 313(25):1557-1563 (Dec. 19, 1985).
Henkin et al., "Niacin Revisited. Clinical Observations on an Important but Underutilized Drug", The American Journal of Medicine, 91:239-246 (Sep. 1991).
Kereaztes, N.A., et al., Pharmazie, 33(1):747-749 (1978).
Kirchstein et al., "Imparied Fibrinolytic Capacity and Tissue Plasminogen Activator Release in Patients with Restenosis and Percutaneous Transluminal Coronary Angioplasty (PTCA)," Thrombosis and Haemostasis, 1989, p. 1 (1 page).
Andreotti, F., et al. "Major Circadian Fluctuations in Fibrinolytic Factors and Possible Relevance to Time of Onset of Myocardial Infarction, Sudden Cardiac Death and Stroke," Am. J. Cardiol., 62:635-637 (1988).
Office Action dated Jan. 24, 2008 in U.S. Appl. No. 11/757,963.
Office Action dated Feb. 12, 2008 in U.S. Appl. No. 11/757,865.
Office Action dated Jul. 9, 2008 in U.S. Appl. No. 11/757,967.
Office Action dated Jan. 4, 2001 in U.S. Appl. No. 09/478,325.
Office Action dated Jun. 20, 2001 in U.S. Appl. No. 09/478,325.
Letter to Applicant from U.S. Department of Health and Human Services dated Jul. 28, 1997.
Complaint—*Abbott Laboratories and Abbott Respiratory LLC* v. *Lupin Limited and Lupin Pharmaceuticals, Inc.*—dated Mar. 6, 2009.
Exhibits A-G for the Complaint—*Abbott Laboratories and Abbott Respiratory LLC* v. *Lupin Limited and Lupin Pharmaceuticals, Inc.*—dated Mar. 6, 2009.
Holmes et al., Drugs Affecting Lipid Metabolism, 1969, "Pyridines Affecting FFA Mobilization In Vivo", pp. 85-90.
Office Action in U.S. Appl. No. 08/962,421 mailed on Oct. 5, 2007.
Office Action in U.S. Appl. No. 08/962,421 mailed on Jun. 14, 2006.
Office Action in U.S. Appl. No. 08/962,421 mailed on Dec. 30, 2005.
Office Action in U.S. Appl. No. 08/962,421 mailed on Jan. 26, 2005.
Office Action in U.S. Appl. No. 08/962,421 mailed on Mar. 19, 2004.
Office Action in U.S. Appl. No. 08/962,421 mailed on May 6, 2003.
Office Action in U.S. Appl. No. 08/962,421 mailed on Mar. 1, 2000.
Office Action in U.S. Appl. No. 08/962,421 mailed on Oct. 2, 1998.
Office Action in U.S. Appl. No. 08/962,027 mailed on Jun. 18, 2003.
Office Action in U.S. Appl. No. 08/962,027 mailed on Jan. 25, 1999.
Office Action in U.S. Appl. No. 08/960,557 mailed on Apr. 3, 2009.
Office Action in U.S. Appl. No. 08/960,557 mailed on Jun. 30, 2008.
Office Action in U.S. Appl. No. 08/960,557 mailed on Mar. 18, 2008.
Office Action in U.S. Appl. No. 08/960,557 mailed on Jun. 14, 2007.
Ex parte Quayle Action in U.S. Appl. No. 08/960,557 mailed on Aug. 15, 2000.
Office Action in U.S. Appl. No. 08/960,557 mailed on Sep. 23, 1998.
Office Action in U.S. Appl. No. 09/470,603 mailed on Feb. 10, 2004.
Office Action in U.S. Appl. No. 09/470,603 mailed on Jun. 4, 2003.
Office Action in U.S. Appl. No. 09/470,603 mailed on May 11, 2001.
Office Action in U.S. Appl. No. 11/496,192 mailed on Dec. 14, 2006.
Office Action in U.S. Appl. No. 11/761,402 mailed on Apr. 23, 2008.
Office Action in U.S. Appl. No. 11/761,402 mailed on Nov. 1, 2007.
Ex parte Quayle Action in U.S. Appl. No. 08/962,422 mailed on May 7, 2003.
Office Action in U.S. Appl. No. 08/962,422 mailed on Jul. 3, 2002.
Office Action in U.S. Appl. No. 08/962,422 mailed on Nov. 15, 2000.
Office Action in U.S. Appl. No. 08/962,422 mailed on Sep. 18, 1998.
Office Action in U.S. Appl. No. 08/962,424 mailed on Mar. 13, 2003.
Office Action in U.S. Appl. No. 08/962,424 mailed on Oct. 23, 2001.
Office Action in U.S. Appl. No. 08/962,424 mailed on Mar. 22, 2001.
Office Action in U.S. Appl. No. 08/962,424 mailed on Sep. 23, 1998.
Office Action in U.S. Appl. No. 10/127,213 mailed on Jul. 28, 2003.
Office Action in U.S. Appl. No. 08/962,423 mailed on Sep. 1, 2000.
Office Action in U.S. Appl. No. 08/962,423 mailed on Sep. 23, 1998.
Interview Summary in U.S. Appl. No. 08/962,422 Jun. dated Jun. 18, 2003 and Notice of Allowability.
Office Action in U.S. Appl. No. 08/814,974 mailed on Mar. 15, 1999.
Office Action in U.S. Appl. No. 08/814,974 mailed on Nov. 23, 1998.
Office Action in U.S. Appl. No. 08/814,974 mailed on Jul. 6, 1998.
Office Action in U.S. Appl. No. 08/814,974 mailed on Dec. 3, 1997.
Office Action in U.S. Appl. No. 08/368,378 mailed on Aug. 26, 1998.
Notice of Allowability and Reasons for Allowance in U.S. Appl. No. 08/962,424 dated Dec. 9, 2002.
Advisory Action in U.S. Appl. No. 08/368,378 mailed on Jun. 10, 1996.
Advisory Action in U.S. Appl. No. 08/368,378 mailed on Apr. 19, 1996.
Suspension Action notice and Interview Summary in U.S. Appl. No. 08/368,378 dated Mar. 19, 1999.
Office Action in U.S. Appl. No. 08/368,378 mailed on Jun. 30, 1995.
Notice of Allowability and Reasons for Allowance in U.S. Appl. No. 08/368,378 dated Jun. 30, 1999.
Interview Summary in U.S. Appl. No. 10/127,213 dated Feb. 19, 2004.
Interview Summary in U.S. Appl. No. 08/814,974 dated Jan. 6, 1999.
Interview Summary in U.S. Appl. No. 08/814,974 dated Aug. 18, 1998.
Interview Summaries in U.S. Appl. No. 08/814,974 dated Sep. 23, 1998 and Oct. 28, 1998.
Office Action in U.S. Appl. No. 08/814,974 dated Jun. 16, 1999.
Suspension Action in U.S. Appl. No. 08/368,378 and Possible Interference dated Nov. 22, 1996.
Notice of Allowability in U.S. Appl. No. 08/962,424 dated Sep. 28, 2000.
Office Action dated Jul. 28, 2003 in U.S. Appl. No. 10/127,213.
Interview Summary dated Feb. 25, 2004 in U.S. Appl. No. 10/127,213.
Office Action dated Nov. 5, 1999 in U.S. Appl. No. 08/814,974.
Office Action dated Jul. 7, 1994 in U.S. Appl. No. 08/124,392.
Office Action dated Nov. 27, 1995 in U.S. Appl. No. 08/368,378.
Studies in the texture and properties of acetylsalicylic acid tablets, Pharmazie 33, Hill (1978) (Translation enclosed).
Barr Laboratories Paragraph IV Certification, dated Nov. 18, 2009.
Lupin Limited Paragraph IV Vertification, dated Jan. 22, 2009.
Sun Pharma Global FZE Paragraph IV Certification, dated Jan. 4, 2010.
Jokubaitis, LA, Fluvastatin in combination with other lipid-lowering agents, Br. J. Clin. Prac. Suppl., 77, pp. 28-32 (1994).
Vacek et al., Comparison of Lovastatin and Nocotinic Acid (1.2g) with either drug alone for the Type II Hyperlipoproteinemia, Am. J. Cardiol., 76(3), 182-184 (1995).
Erkelens, DW, Combination drug therapy with HMG CoA Reductase Inhibitors and bile aced sequesterants for Hypercholesterolemia, Cardiology, 77, Suppl. 4, pp. 33-38 (1990).
Office action in U.S. Appl. No. 10/260,027, dated Apr. 29, 2008.
Office action in U.S. Appl. No. 10/260,027, dated Jul. 26, 2007.
Office action in U.S. Appl. No. 11/071,099, dated Jan. 20, 2006.
Office action in U.S. Appl. No. 11/071,099, dated Feb. 6, 2008.
Office action in U.S. Appl. No. 11/071,099, dated Apr. 30, 2007.
Office action in U.S. Appl. No. 11/071,099, dated Jul. 10, 2006.
Office action in U.S. Appl. No. 11/071,099, dated Oct. 17, 2007.
Office action in U.S. Appl. No. 11/071,099, dated Nov. 18, 2008.
Office action in U.S. Appl. No. 11/071,099, dated Dec. 22, 2009.
Office action in U.S. Appl. No. 11/705,675, dated Jan. 8, 2009.
Office action in U.S. Appl. No. 12/194,051, dated Aug. 9, 2010.

Office action in U.S. Appl. No. 12/194,051, dated Oct. 13, 2009.
Office action in U.S. Appl. No. 08/903,752, dated Dec. 17, 2001.
Office action in U.S. Appl. No. 08/903,752, dated Mar. 14, 2001.
Office action in U.S. Appl. No. 08/903,752, dated Dec. 17, 1999.
Office action in U.S. Appl. No. 08/903,752, dated Jun. 10, 1999.
Office action in U.S. Appl. No. 08/903,752, dated Sep. 24, 1998.
Office action in U.S. Appl. No. 08/903,871, dated Dec. 15, 2001.
Office action in U.S. Appl. No. 08/903,871, dated Feb. 27, 2001.
Office action in U.S. Appl. No. 08/903,871, dated Jun. 12, 2000.
Office action in U.S. Appl. No. 08/903,871, dated Aug. 30, 1999.
Office action in U.S. Appl. No. 08/903,871, dated May 21, 1998.
Ansel et al., Pharmaceutical Dosage Forms and Drug Delivery Systems, 6th Ed. (1995), pp. 2 and 213.
Excerpt from Guidance for Industry: Bioavailability and Bioequivalence Studies for Orally administered Drug Products-General Considerations (2003), pp. 1-23.
Excerpt from New Webster's Dictionary and Thesaurus (1993), p. 636.
Excerpt from Stedman's Medical Dictionary, 25th Ed. (1990), p. 1778.
Excerpt from the Dictionary of Pharmacy, (1986), p. 96 and 290.
Excerpt from United States Pharmacopeia 24 & National Formulary 19, p. 1177, monograph for niacin tablets, 2000.
Saito et al., Comparison between morning and evening doses of simvastatin in hyperlipidemic patients, Arteriosclerosis and Thrombosis, 1991.
Jokubaitis, LA, Fluvastatin in combination with other lipid-lowering agents, Br. J. Clin. Prac. Suppl., 77, pp. 28-32 (1994).
Vacek et al., Comparison of Lovastatin and Nicotinic Acid (1.2g) with either drug alone for Type II Hyperlipoproteinemia, Am. J. Cardiol., 76(3), 182-184 (1995).
Erkelens, DW, Combination drug therapy with HMG CoA Reductase Inhibitors and bile acid sequestrants for hypercholesterolemia, Cardiology, 77, Supp. 4, pp. 33-38 (1990).
Office Action in U.S. Appl. No. 12/187,954 mailed Jun. 14, 2010.
Office Action in U.S. Appl. No. 12/187,954 mailed Oct. 28, 2009.
Office Action in U.S. Appl. No. 11/757,959 mailed Oct. 29, 2009.
Office Action in U.S. Appl. No. 11/757,959 mailed Jun. 15, 2010.
Office Action in U.S. Appl. No. 11/839,431 mailed Oct. 28, 2009.
Office Action in U.S. Appl. No. 11/839,431 mailed Jun. 14, 2010.
Office Action in U.S. Appl. No. 12/187,960 mailed Jun. 14, 2010.
Office Action in U.S. Appl. No. 12/187,960 mailed Oct. 28, 2009.
Office Action in U.S. Appl. No. 12/423,027 mailed Oct. 29, 2009.
Office Action in U.S. Appl. No. 08/960,557 dated Jan. 15, 2010.
Office Action in U.S. Appl. No. 08/960,557 dated Jun. 14, 2007.
Office Action in U.S. Appl. No. 11/496,192 dated Jul. 2, 2007.
Office Action in U.S. Appl. No. 11/757,963 dated Feb. 12, 2008.
Office Action in U.S. Appl. No. 11/757,965 dated Jan. 24, 2008.
Office Action in U.S. Appl. No. 11/761,402 dated Apr. 23, 2008.
Office Action in U.S. Appl. No. 11/761,402 dated Nov. 1, 2007.
Office Action in U.S. Appl. No. 12/197,208 dated Apr. 20, 2009.
Excerpts from United States Pharmacopeia XXII (1989), pp. 6, 1579, 1618, 1688-1697, and 1710-1712.
Excerpts from United States Pharmacopeia 23 & National Formulary 18 (1995), pp. 8, 1792, 1838-1839, 1940-1951, and 1982-1984.
Excerpt from Webster's Ninth New Collegiate Dictionary (1983), p. 355.
Ansel et al., Pharmaceutical Dosage Forms and Drug Delivery Systems, 6th Ed. (1995), pp. 110-116.
Excerpt from Pharmaceutics: The Science of Dosage Form Design, (1988), pp. 307-317.
Excerpt from Pharmaceutical Dosage Forms, edited by Lieberman et al., (1980), pp. 112-147.
Excerpt from Sprowl's American Pharmacy, edited by Dittert, 7th Ed. (1974), pp. 354-361.
Mylan Paragraph IV Certification for Simcor, dated May 14, 2010.
Barr Laboratories Paragraph IV Certification for Simcor, dated Nov. 18, 2009.
Lupin Limited Paragraph IV Certification for Niaspan, dated Jan. 22, 2009.
Sun Pharma Global FZE Paragraph IV Certification for Niaspan, dated Jan. 4, 2010.
Watson Laboratories Paragraph IV Certification for Simcor, dated Mar. 25, 2010.
Sandoz Paragraph IV Certification for Niaspan, dated May 5, 2010.
Sun Pharmaceutical Industries, Inc. Paragraph IV Certification for Niaspan, dated Apr. 21, 2010.
Teva Pharmaceuticals Paragraph IV Certification for Simcor, dated Jul. 26, 2010.
Barr Laboratories, Inc. Paragraph IV Certification for Advicor, dated Dec. 18, 2008.
Teva Pharmaceuticals Paragraph IV Certification for Simcor, dated Mar. 1, 2010.
Teva Pharmaceuticals Paragraph IV Certification for Simcor, dated Dec. 8, 2009.
Barr Laboratories, Inc. Paragraph IV Certification for Advicor, dated Aug. 13, 2008.
Barr Laboratories, Inc. Paragraph IV Certification for Advicor, dated Sep. 19, 2008.
Barr Laboratories Paragraph IV Certification for Niaspan, dated Jan. 15, 2002.
*Abbott Labs.* v. *Mylan Inc.*, D.Del., 1:10-CV-00559-SLR; Abbott's Complaint, dated May 28, 2010.
*Abbott Labs.* v. *Mylan Inc.*, D.Del., 1:10-CV-00559-SLR; Mylan's Answer and Counterclaims, dated Aug. 23, 2010.
*Abbott Labs.* v. *Mylan Inc.*, D.Del., 1:10-CV-00559-SLR; Abbott's Answer to Mylan's Counterclaims, dated Sep. 13, 2010.
*Abbott Labs.* v. *Teva Pharmaceutical Industries, Ltd.*, D.Del., 1:10-CV-00766; Abbott's Complaint, dated Sep. 8, 2010.
*Abbott Labs.* v. *Sandoz Inc.*, D.Del., 1:10-CV-00538-SLR; Abbott's Complaint, dated Jun. 18, 2010.
*Abbott Labs.* v. *Sandoz Inc.*, D.Del., 1:10-CV-00538-SLR; Sandoz Answer and Counterclaims, dated Aug. 20, 2010.
*Abbott Labs.* v. *Sandoz Inc.*, D.Del., 1:10-CV-00538-SLR; Abbott's Answer to Counterclaims, dated Sep. 15, 2010.
*Abbott Labs.* v. *Sun Pharmaceutical Industries, Ltd.*, D.Del., 1:10-CV-00112-SLR-MPT; Abbott's Complaint, dated Feb. 12, 2010.
*Abbott Labs.* v. *Sun Pharmaceutical Industries, Ltd.*, D.Del., 1:10-CV-00112-SLR-MPT; Sun's Answer, dated Apr. 1, 2010.
*Abbott Labs.* v. *Sun Pharmaceutical Industries, Ltd.*, D.Del., 1:10-CV-00488-SLR; Abbott's Complaint, dated Jun. 4, 2010.
*Abbott Labs.* v. *Sun Pharmaceutical Industries, Ltd.*, D.Del., 1:10-CV-00488-SLR; Sun's Answer, dated Jun. 28, 2010.
Excerpt from 1997 Physician's Desk Reference, p. 2767.
Upsher-Smith's Internet Advertisement at http://www.upsher-smith.com/sloniacin.html.
Upsher-Smith's OTC Labels for 750mg, 500mg, and 250mg Slo-Niacin OTC products.
Wu et al., "Promotion of Extended-Release Niacin Tablets at a Veterans Affairs Medical Center", Am. J. Hosp. Pharm., 47:2031-2034 (1990).
Medical Science Bulletin, "The Toxicity of Niacin", https://pharminfo.com/publs/msb/niacin.html.
McKenney et al., A Comparison of the Efficacy and Toxic Effects of Sustained- vs. Immediate-Release Niacin in Hypercholesterolemic Patients. JAMA, 271(9):672-677 (1994).
199 USPQ 824 (*Endo Laboratories, Inc.* v. *Fredericks*, Aug. 18, 1978).
Gray, D.R., et al., "Efficacy and Safety of Controlled-Release Niacin in Dyslipproteinemic Veterans," Ann. Intern. Med. 121:252-258 (1994).
Keenan et al., "A Clinical Trial of Oat Bran and Niacin in the Treatment of Hyperlipidemia", Journal Fam. Prac., 24(3), 313-319 (1992).
"Report of the National Cholesterol Education Program Expert Panel on Detection, Evaluation and Treatment of High Blood Cholesterol in Adults", The Expert Panel, Arch. Intern. ,148(1), 36-39 1988.
Wiman, B., et al., "The Role of Fibinolytic System in Deep Vein Thrombosis", J. Lab. Clin. Med., 105(2):265-270 (1985).
Angleton et al., "Diurnal Variation of Tissue-Type Pasminogen Activator and its Rapid Inhibitor (PAI-1)" Circulation, 79:101-106 (1989).
*KOS Pharmaceuticals* v. *Barr Laboratories*-Reply to Counterclaims and Counterclaims for Declaratory Judgment (Case No. 02CV1683 (Consolidated with Cases 02 CV 6409 and 8995)).

*KOS Pharmaceuticals* v. *Barr Laboratories*-Barr Laboratories' Answer, Affirmative Defenses and Counterclaims to Complaint (Case No. 02CV6400).
*KOS Pharmaceuticals* v. *Barr Laboratories*-Complaint (Case No. 02CV6409).
*KOS Pharmaceuticals* v. *Barr Laboratories*-Barr Laboratories' Amended Answer, Affirmative Defenses and Counterclaims to First Amended Complaint (Case No. 02CV1683).
*KOS Pharmaceuticals* v. *Barr Laboratories*-Reply to Counterclaims (02 CV 1683).
*KOS Pharmaceuticals* v. *Barr Laboratories*-Barr Laboratories' Answer, Affirmative Defenses and Reply to Counterclaims to First Amended Complaint (02 CV 1683).
*KOS Pharmaceuticals* v. *Barr Laboratories*—Complaint (02 CV 1683).
*KOS Pharmaceuticals* v. *Barr Laboratories*—Complaint (02 CV 8995).
*KOS Pharmaceuticals* v. *Barr Laboratories*—First Amended Complaint (02 CV 1683).
*KOS Pharmaceuticals* v. *Barr Laboratories*-Barr Laboratories' Answer, Affirmative Defenses and Counterclaims to Complaint (02 CV 8995).
FDA Warning letter to KOS re: Niaspan.
PDR from 1988 showing Niaplus.
Earthman et al., Southern Medical J. Apr. 1991 84(4) 496-7. Lactic Acidosis associated with High-Dose Niacin Therapy.
McCarthy on Trademarks, Section 19:110.
Trademark U.S. Appl. No. 73/838,497.
Carlson, L., et al., "Effect of a Single Dose of Nicotinic Acid on Plasma Lipids in Patients with Hyperlipoproteinemia", Acta Med. Scand. vol. 183:457-465 (1968).
Hodis, H.N. "Acute Hepatic Failure Associated with the Use of Low-Dose Sustained-Release Niacin", Letters to the Editors, JAMA, 264(2):181 (1990).
Search Report on Niacin Lotions.
Andreotti, F., et al., American Journal of Cardiology, 635-637 (1998).
Ann of Intern Med, 114, 224-237 (1991).
LaRosa, et al., Circulation, 81(5), 1721-1733 (1990).
Remingtons Pharmaceutical Sciences, 1304-1323 and 1676-1686, Mack Publishing Co, Easton , Pa (1990).
Renzetti, A.R., et al., J. Pharm. Pharmacol., 37, 906-909 (1985).
Salomon JL et al, Pharm. Acta Helv., 54(3), p. 75-85, 1979.
Yusek, et al., JAMA, 260(15), 2259-2263 (1988).
Zimmerman, et al, Hepatotoxicity, 510-522 (1978).
Dow, Formulating for Controlled Release with Methocel Premium Cellulose Ethers,Dow Chemical Company publications, 1-33 (1995).
Dow, Methocel as a Binding Agent for Tablet production by Wet Granulation, Dow Chemical Company publication, 1-15 (1985).
Dow, Technical Information Methods of Formulating Controlled Release Products Outside the Forest Lab Patent US 4,389,393 Claims.
Ljungberg et al., "The role of the Fibrinolytic system in deep vein thromobosis" from departments of Karolinska Hospital (1 page) Oct. 1984.
Muller et al., "Circadian variation in the frequence of sudden cardiac death," Pathophysiology and Natural History, 75 (1) (Jan. 1987).
Ross, "The Pathogenesis of Atherosclerosis—An Update," The New England Journal of Medicine, 314(8):488-500 (Feb. 20, 1986).
Sprengers et al., "Plasminogen Activator Inhibitors," Blood, 69(2):381-387 (Feb. 1987).
Squires, R.W. et al., Mayo Clin. Proc., 67:855-860, 1992.
Japanese Patent JP633310827 A 881219 DW8905 (translated).
Japanese Patent JP3221854 A 930831 DW9339 A61K9/22 (translated).
*Abbott Labs.* v. *Lupin Ltd.*, D. Del., 1:09CV00152-JJF-LPS; Supplemental declaration of Bruce Stoner, dated Mar. 29, 2010.
*Abbott Labs.* v. *Lupin Ltd.*, D. Del., 1:09CV00152-JJF-LPS; Supplemental declaration of James McGinnity, dated Mar. 29, 2010 [Redacted].
*Abbott Labs.* v. *Lupin Ltd.*, D. Del., 1:09CV00152-JJF-LPS; Lupin second supplemental response to interrogatories, dated May 12, 2009.
*Abbott Labs.* v. *Lupin Ltd.*, D. Del., 1:09CV00152-JJF-LPS; Lupin claim chart for response to first supplemental response to interrogatories.
*Abbott Labs.* v. *Lupin Ltd.*, D. Del., 1:09CV00152-JJF-LPS; Response to first set of interrogatories, dated Sep. 4, 2009.
*Abbott Labs.* v. *Lupin Ltd.*, D. Del., 1:09CV00152-JJF-LPS; Report regarding claim construction, dated Jun. 18, 2010.
*Abbott Labs.* v. *Lupin Ltd.*, D. Del., 1:09CV00152-JJF-LPS; Supplemental declaration of Thomas Foster, dated Mar. 29, 2010.
*Abbott Labs.* v. *Lupin Ltd.*, D. Del., 1:09CV00152-JJF-LPS; Appendix in support of Lupin opening and answering briefs, dated Apr. 5, 2010 [Redacted].
*Abbott Labs.* v. *Lupin Ltd.*, D. Del., 1:09CV00152-JJF-LPS; Chart of disputed claim terms, dated Apr. 5, 2010.
*Abbott Labs.* v. *Lupin Ltd.*, D. Del., 1:09CV00152-JJF-LPS; Claim charts for Lupin's first supplemental response to Abbott Interrogatories Nos. 4-10 and 12.
*Abbott Labs.* v. *Lupin Ltd.*, D. Del., 1:09CV00152-JJF-LPS; Declaration of David Taft, dated Feb. 28, 2010.
*Abbott Labs.* v. *Lupin Ltd.*, D. Del., 1:09CV00152-JJF-LPS; Declaration of Frank Sacks, dated Mar. 1, 2010, in support of Plaintiff's opening claim construction.
*Abbott Labs.* v. *Lupin Ltd.*, D. Del., 1:09CV00152-JJF-LPS; Declaration of Ronald Wharton, dated Feb. 26, 2010.
*Abbott Labs.* v. *Lupin Ltd.*, D. Del., 1:09CV00152-JJF-LPS; Declaration of Bruce Stoner, dated Mar. 1, 2010.
*Abbott Labs.* v. *Lupin Ltd.*, D. Del., 1:09CV00152-JJF-LPS; Declaration of James McGinnity, dated Mar. 1, 2010.
*Abbott Labs.* v. *Lupin Ltd.*, D. Del., 1:09CV00152-JJF-LPS; Declaration of Thomas Foster, dated Mar. 1, 2010.
*Abbott Labs.* v. *Lupin Ltd.*, D. Del., 1:09CV00152-JJF-LPS; Plaintiff's opening claim construction brief, dated Mar. 1, 2010.
*Abbott Labs.* v. *Lupin Ltd.*, D. Del., 1:09CV00152-JJF-LPS; Plaintiff answering claim construction brief, dated Mar. 29, 2010.
*Abbott Labs.* v. *Lupin Ltd.*, D. Del., 1:09CV00152-JJF-LPS; Deposition of David Bova, dated Dec. 17, 2009 [Redacted].
*Abbott Labs.* v.*Lupin Ltd.*, D. Del., 1:09CV00152-JJF-LPS; Answer brief, dated Mar. 29, 2010 [Redacted].
*Abbott Labs.* v. *Lupin Ltd.*, D. Del., 1:09CV00152-JJF-LPS; Lupin's opening brief concerning claim construction, dated Mar. 1, 2010 [Redacted].
*Abbott Labs.* v. *Lupin Ltd.*, D. Del., 1:09CV00152-JJF-LPS; Plaintiff answer with claim chart, dated Mar. 29, 2010.
*Abbott Labs.* v. *Lupin Ltd.*, D. Del., 1:09CV00152-JJF-LPS; Expert report of David Taft, Ph.D., dated Aug. 30, 2010.
*Abbott Labs.* v. *Lupin Ltd.*, D. Del., 1:09CV00152-JJF-LPS; Expert report of Robert Wharton, M.D., dated Aug. 31, 2010.
*Abbott Labs.* v. *Lupin Ltd.*, D. Del., 1:09CV00152-JJF-LPS; Expert report of Gilbert Fleming, M.D., dated Aug. 30, 2010.
*Abbott Labs.* v. *Lupin Ltd.*, D. Del., 1:09CV00152-JJF-LPS; Expert report of Kathryn Zunich, M.D., dated Aug. 27, 2010.
*Abbott Labs.* v. *Lupin Ltd.*, D. Del., 1:09CV00152-JJF-LPS; Expert report of Walter Chambliss, Ph.D., dated Aug. 30, 2010.
*Abbott Labs.* v. *Lupin Ltd.*, D. Del., 1:09CV00152-JJF-LPS; Lupin's First Supplemental Response to Abbott Interrogatories Nos. 4-10 and 12 [Redacted], dated Apr. 22, 2010.
*Abbott Labs.* v. *Lupin Ltd.*, D. Del., 1:09CV00152-JJF-LPS; Abbott Request for Clarification of Claim Construction, dated Jul. 2, 2010.
*Abbott Labs.* v. *Lupin Ltd.*, D. Del., 1:09CV00152-JJF-LPS; Lupin Objections to Claim Construction, dated Jul. 2, 2010.
*Abbott Labs.* v. *Lupin Ltd.*, D. Del., 1:09CV00152-JJF-LPS; Lupin's Response to Request for Clarification of Claim Construction, dated Jul. 12, 2010.
*Abbott Labs.* v.*Lupin Ltd.*, D. Del., 1:09CV00152-JJF-LPS; Abbott's Response to Lupin's Objections to Claim Construction, dated Jul. 16, 2010.
*Abbott Labs.* v. *Lupin Ltd.*, D. Del., 1:09CV00152-JJF-LPS; Lupin's Motion for Clarification of Claim Construction, dated Jul. 27, 2010.
*Abbott Labs.* v. *Lupin Ltd.*, D. Del., 1:09CV00152-JJF-LPS; Claim Construction Order, dated Jul. 30, 2010.
*Abbott Labs.* v. *Teva Pharmaceutical Industries Ltd.*, D. Del., 1:10CV00057-UNA; Abbott's Complaint, dated Jan. 22, 2010.

*Abbott Labs.* v. *Teva Pharmaceutical Industries Ltd.*, D. Del., 1:10CV00057-UNA; Abbott's Amended Complaint, dated Jan. 25, 2010.
*Abbott Labs.* v. *Teva Pharmaceutical Industries Ltd.*, D. Del., 1:10CV00057-UNA; Teva's Answer to the Amended Complaint, dated Mar. 9, 2010.
*Abbott Labs.* v. *Teva Pharmaceutical Industries Ltd.*, D. Del., 1:10CV00057-UNA; Teva's Answers to Abbott's First Set of Interrogatories; dated Sep. 10, 2010.
*Abbott Labs* v. *Watson Pharmaceuticals, Inc.*, D.Del., 1:10CV00373-UNA; Abbott's Complaint, dated May 4, 2010.
*Abbott Labs* v. *Watson Pharmaceuticals, Inc.*, D.Del., 1:10CV00373-UNA; Watson's Answers and Counterclaims, dated May 25, 2010.
*Abbott Labs* v. *Watson Pharmaceuticals, Inc.*, D.Del., 1:10CV00373-UNA; Abbott's Answer to Counterclaims, dated Jun. 15, 2010.
*Abbott Labs* v. *Watson Pharmaceuticals, Inc.*, D.Del., 1:10CV00373-UNA; Watson's Answers to Abbott's First Set of Interrogatories, dated Sep. 10, 2010.
*Abbott Labs.* v. *Teva Pharmaceutical Industries Ltd.*, D. Del., 1:10CV00302-SLR; Abbott's Complaint, dated Apr. 14, 2010.
*Abbott Labs.* v. *Teva Pharmaceutical Industries Ltd.*, D. Del., 1:10CV00302-SLR; Teva's Answer to Complaint, dated May 6, 2010.
*Abbott Labs.* v. *Lupin Ltd.*, 09-cv-00152-LPS; Additional Expert Report of Ronald H. Wharton, M.D., Regarding Newly Asserted Claims 13 and 14 in the '967 Patent with Accompanying Claim Charts, dated Nov. 2, 2010 (Redacted). Subject to Protective Order.
*Abbott Labs.* v. *Lupin Ltd.*, 09-cv-00152-LPS; Rebuttal Expert Report of Michael B. Bottorff, Pharm.D., dated Dec. 17, 2010. **Subject to Protective Order*.
*Abbott Labs.* v. *Lupin Ltd.*, 09-cv-00152-LPS; Rebuttal Expert Report of James W. McGinnity, Ph.D., dated Dec. 17, 2010 (Redacted). Subject to Protective Order.
*Abbott Labs.* v. *Lupin Ltd.*, 09-cv-00152-LPS; Rebuttal Expert Report of Mark A. Munger, Pharm.D., dated Dec. 17, 2010 (Redacted). Subject to Protective Order.
*Abbott Labs.* v. *Lupin Ltd.*, 09-cv-00152-LPS; Rebuttal Expert Report of Frank Sacks, M.D., dated Dec. 17, 2010 (Redacted). Subject to Protective Order.
*Abbott Labs.* v. *Watson Labs, Inc.*, 10-cv-00057-SLR-MPTI; Watson's First Supplemental Answers to Interrogatories Nos. 5-10, dated Nov. 15, 2010.
*Abbott Labs.* v. *Teva Pharm.*, 10-cv-00057-SLR-MPT; Teva's First Supplemental Answers to Interrogatories Nos. 5-9, dated Nov. 15, 2010.
*Abbott Labs.* v. *Teva Pharm. Indus. Ltd.*, 1:10CV00057-SLR-LPS; Plaintiff's First Supplemental Responses to Defendant's First Set of Interrogatories, dated Dec. 15, 2010.
*Abbott Labs.* v. *Lupin Ltd.*, D. Del., 1:09CV00152-LPS; Reply Expert Report of Gilbert Alexander Fleming, M.D., dated Jan. 21, 2011. **Subject to Protective Order*.
*Abbott Labs.* v. *Lupin Ltd.*, D. Del., 1:09CV00152-LPS; Reply Expert Report of David R. Taft, Ph.D., dated Jan. 25, 2011. Subject to Protective Order.
*Abbott Labs.* v. *Lupin Ltd.*, D. Del., 1:09CV00152-LPS; Reply Expert Report of Kathryn M. Zunich, M.D., dated Jan. 18, 2011. Subject to Protective Order.
*Abbott Labs.* v. *Lupin Ltd.*, D. Del., 1:09CV00152-LPS; Reply Expert Report of Ronald H. Wharton, M.D., dated Jan. 24, 2011 (Redacted). Subject to Protective Order.
*Abbott Labs.* v. *Lupin Ltd.*, D. Del., 1:09CV00152-LPS; Reply Expert Report of Walter G. Chambliss, Ph.D., dated Jan. 21, 2011. **Subject to Protective Order*.
Teva Pharmaceuticals Paragraph IV Certification for Simcor 1000 mg/40 mg dated Feb. 4, 2011.
Sandoz Inc. Paragraph IV Certification for Niaspan, 1000mg, 750mg and 500mg dated Jan. 3, 2011.
Watson Laboratories, Inc. Paragraph IV Certification for Simcor 500 mg/40 mg dated Feb. 9, 2011.

*Abbott Labs.* v. *Sun Pharm. Indus. Ltd.* D. Del., 1:10-CV-00112-SLR-MPT; Defendant Sun's Supplemental Answers to Plaintiffs' First and Second Interrogatories to Defendants (Nos. 5-10, 12-13) dated Feb. 11, 2011.
*Abbott Labs.* v. *Teva Pharm. Indus. Ltd. and Watson Labs. Inc.*, 1:10CV00057-SLR-MPT; Defendants' Identification of Claim Terms Requiring Construction and Proposed Claim Constructions, dated Jan. 21, 2011.
*Abbott Labs.* v. *Teva Pharm. Indus. Ltd. and Watson Labs. Inc.*, 1:10CV00057-SLR-MPT; Plaintiffs' Proposed Claim Terms for Construction and Proposed Constructions, dated Jan. 21, 2011.
*Abbott Labs.* v. *Teva Pharm. Indus. Ltd. and Watson Labs. Inc.*, 1:10CV00057-SLR-LPS; Abbott's Third Supplemental Response to Teva/Watson [Joint Defendants] first set of joint interrogatories, dated Mar. 15, 2011.
*Abbott Labs.* v. *Teva Pharm. Indus. Ltd. and Watson Labs. Inc.*, 1:10CV00057-SLR-LPS; Abbott's Second Supplemental Response to Teva/Watson [Joint Defendants] First Set of Joint Interrogatories, dated Mar. 11, 2011.
*Abbott Labs.* v. *Sun Pharm. Indus. Ltd.* D. Del., 1:10-CV-00112-SLR; Abbott's First Supplemental Response to Interrogatories, dated Mar. 14, 2011. (Redacted).
*Abbott Labs.* v. *Sun Pharm. Indus. Ltd.* D. Del., 1:10-CV-00488-SLR; Sun's Proposed Claim Construction, dated Mar. 21, 2011.
*Abbott Labs.* v. *Teva Pharm. Indus. Ltd.*, D.Del., 1:11-CV-00239; Complaint regarding Simcor 1000mg/40mg, dated Mar. 21, 2011.
*Abbott Labs.* v. *Teva Pharm. Indus. Ltd. and Watson Labs. Inc.*, 1:10CV00057-SLR-MPT; Supplemental Answer to Interrogatory No. 12, dated Mar. 24, 2011 Subject to Protective Order.
*Abbott Labs.* v. *Watson Labs. Inc.*, D.Del., 1:11-CV-00251; Complaint regarding Simcor 500mg/40mg, dated Mar. 25, 2011.
*Abbott Labs.* v. *Sun Pharm. Indus. Ltd.* D. Del., 1:10-CV-00488-SLR; Abbott's Proposed Claim Construction, dated Mar. 21, 2011.
*Abbott Labs.* v. *Lupin Ltd.*, 09-cv-00152-LPS; Abbott's Motion of Summary Judgment of No Invalidity of US Patent No. 6,080,428 for Double Patenting.
*Abbott Labs.* v. *Lupin Ltd.*, 09-cv-00152-LPS; Lupin's Motion of Summary Judgment of Invalidity of US Patent No. 6,080,428.
*Abbott Labs.* v. *Lupin Ltd.*, 09-cv-00152-LPS; Opening Brief in Support of Abbott's Motion for Summary Judgment of Invalidity of U.S. Patent 6,080,428 for Double Patenting.
*Abbott Labs.* v. *Lupin Ltd.*, 09-cv-00152-LPS; Abbott's Opposition to Lupin's Motion for Summary Judgment of Invalidity of the '428 Patent.
*Abbott Labs.* v. *Lupin Ltd.*, 09-cv-00152-LPS; Lupin's Answering Brief in Opposition to Abbott's Summary Judgment Motion of No Invalidity Due to Double Patenting.
*Abbott Labs.* v. *Lupin Ltd.*, 09-cv-00152-LPS; Reply in Support of Abbott's Motion for Summary Judgment of No Invalidity of U.S. Patent No. 6,080,428 for Double Patenting.
*Abbott Labs.* v. *Lupin Ltd.*, 09-cv-00152-LPS; Lupin's Reply Brief in Support of Its Motion for Summary Judgment of Invalidity of the '428 Patent.
*Abbott Labs.* v. *Lupin Ltd.*, 09-cv-00152-LPS; Memorandum Opinion.
*Abbott Labs.* v. *Sun Pharm. Indus. Ltd.* D. Del., 1:10-CV-00112-SLR; Joint Joint Stipulation of Claim Construction dated Apr. 15, 2011.
*Abbott Labs.* v. *Teva Pharm. Indus. Ltd. and Watson Labs. Inc.*, 10-CV-057-SLR-MPT; Defendants' Teva Pharmaceutials USA, Inc. and Teva Pharmaceutical Industries Ltd. First Amended Answer and Affirmative Defenses to Complaint dated Apr. 14, 2011.
*Abbott Labs.* v. *Teva Pharm. Indus. Ltd. and Watson Labs. Inc.*, 10-057-SLR-MPT; Defendant Watson Laboratories, Inc.—Florida's First Amended Answer, Affirmative Defenses and Counterclaims to Plaintiffs' Complaint dated Apr. 14, 2011.
*Abbott Labs.* v. *Watson Labs, Inc.*, 10-cv-00057-SLR-MPT; Watson's Supplemental Answer to Interrogatory No. 12 dated Mar. 24, 2011 Subject to Protective Order.
*Abbott Labs.* v. *Teva Pharm. Indus. Ltd.*, D.Del., 1:11-CV-00239; Teva's Supplemental Answer to Interrogatory Nos. 1, 2 and 12 dated Mar. 23, 2011 Subject to Protective Order.

*Abbott Labs.* v. *Teva Pharm. Indus. Ltd.*, D.Del., 1:11-CV-00239; Teva's Supplemental Answer to Interrogatory Nos. 5-9 dated Apr. 22, 2011 **Subject to Protective Order*.
*Abbott Labs.* v. *Teva Pharm. Indus. Ltd.*, D.Del., 1:11-CV-00239; Teva/Watson's First Amended Answers, Affirmative Defenses and Counterclaims dated Apr. 11, 2011.
*Abbott Labs.* v. *Watson Labs, Inc.*, 10-cv-00057-SLR-MPT; Watson's Second Supplemental Answer to Interrogatories No. 4-10 dated Apr. 22, 2011.
Watson Paragraph IV letter dated May 25, 2011.
*Abbott Labs.* v. *Sun Pharm. Indus. Ltd.* D. Del., 1:10-CV-00488-SLR; Sun's Objections and Second Supplemental Answer to Plaintiff's Interrogatory No. 6.
*Abbott Labs.* v. *Sun Pharm. Indus. Ltd.* D. Del., 1:10-CV-00488-SLR; Sun's Joint Stipulation on Claim Construction for the Sun case dated Apr. 15, 2011.
*Abbott Labs.* v. *Sun Pharm. Indus. Ltd.* D. Del., 1:10-CV-00488-SLR; Plaintiff's Responses to Third Set of Interrogatories (Nos. 13-22), dated Jun. 16, 2011.
*Abbott Labs.* v. *Lupin Ltd.*, 09-cv-00152-LPS; Memorandum of Opinion dated May 19, 2011.
Stern et al., "Differences in Metabolism of Time-Release and Unmodified Nicotinic Acid: Explanantion of the Differences in Hypolipidemic Action?" Metabolism, vol. 41, No. 8: 879-881 (1992).
Philips and Lightman, "Is Cutaneous Flushing Prostaglandin Mediated" The Lancet, 8223: 754-756 (1981).
Ferrera S. Moncada, "Indomethacin and aspirin abolish prostaglandin release from the spleen," Nat News Biol, 231 (25): 237-239 (1979).
Whelan et al., "The Effect of Aspirin on Niacin-Induced Cutaneous Reactions," J. Fam. Practice 34: 165-168 (1992).
Ivanovskaya E.A. et al., 1998, Molecular-Biological Problems of Drug Design and Mechanism of Drug Action: Pharmacokinetics of Enduracin, Pharm.Chem. J., 32(11): 569-570.
Poon, I.O. et al., 2006, Dissolution Profiles of Nonprescription Extended-Release Niacin and Inositol Niacinate Products, Am. J. Health Sys. Pharm., 63(21):2128-34 at 2131.
Davignon, J et al., 1994, Comparative Efficacy and Safety of Pravastatin, Nicotinic Acid, and the Two Combined in Patients with Hypercholesterolemia, Am. J. Cardiol., 73(5): 339-45.
U.S. FDA's Guidance for Industry SUPAC-MR (1997) ("FDA's Guidance").
O'Reilly P.O. et al., 1959, Sustained Release Nicotinic Acid (Nicospan): Effect on (1) Cholesterol Levels and (2) Leukocytes, Can. Med. Assoc. J., 80(5): 359-62.
The Physician Desk Reference (1992) 46th Ed. At page 1846 for Nicobid.
The Physicians' Desk Reference (1989) 43rd Ed., at 2194 for Slo-Niacin.
Dunn et al., Am. J. Ther. 2, 478-80 (1995).
Handbook of Pharmaceutical Excipients, 2nd Ed., 1994, Excerpts for "Hydroxypropylmethylcellulose at pp. 229-232; "Magnesium Stearate" at pp. 280-282; "Povidone at pp. 392-399; and "Stearic acid" at pp. 494-497.
M Brown & J. Goldstein, The Pharmacological Basis of Therapeutics, 874, 893: (Gilman et al. eds.) 8th Ed. (1990).
Handbook of Pharmaceutical Excipients, 1986, Excerpt for "Hydroxypropylmethylcellulose" at pp. 138-140.
Handbook of Pharmaceutical Excipients, 1986, Excerpt for "Stearic acid" at pp. 298-300.
G. N. Gaut et al., Oral Glucose Tolerance, Plasma Insulin, and Uric Acid Excretion, in Man During Chronic Administration of Nicotinic Acid, 220 Metabolism 1031 (1971).
Carlson L.A. & Olsson A.G., Effect of Hyperlipidemic Drugs on Serum Lipoproteins, in Progress in Biochemical Pharmacology 238, 244 (S. Eisenberg ed. 1979).
Molnar G.D. et al., The Effect of Nicotinic Acid in Diabetes Mellitus, 13 Metabolism 181, 186 (1964).
"Magnesium Stearate," in Handbook of Pharmaceutical Excipients 173 (Am. Pharmaceutical Assoc. ed., 1986).
Gurakar A, et al., "Levels of Lipoprotein Lp(a) Decline with Neomycin and Niacin Treatment," 57 Atherosclerosis 293, 296, 299 (1985).
Gardner S.F. et al, Combination Therapy with low-Dose Lovastatin and Niacin is as Effective as Higher-Dose Lovastatin, 16(3) Pharmacotherapy, 419-23 (1996).
O'Keefe J.H. et al., Effects of Pravastatin with Niacin or Magnesium of Lipid Levels and Postprandial Lipemia, 76 Am. J. Cardiol., 480-84 (1995).
Pasternak RC et al., Effect of Combination Therapy with Lipid-Reducing Drugs in Patients with Coronary Heart Disease and "Normal" Cholesterol Levels, 125(7) Ann. Intern. Med., 529-40 (1996).
Stein E.A. et al., Efficacy and Tolerability of Low-dose Simvastatin and Niacin, Alone and in Combination, in Patients with Combined Hyperlipidemia: A Prospective Trial, 1(2) J. Cardiovasc. Pharmacol. Therapeut., 107-16 (1996).
Impax Laboratories Inc., Paragraph IV Certification for Simcor, dated Oct. 13, 2010.
Progress in Biochemical Pharmacology, "Effect of Drugs on Lipoprotein Metabolism", Progress in Biochemical Pharmacology, vol. 15, pp. 238-257 (Karger, Basel 1979).
FDA letter regarding Nia-trol 500 mg caplets, dated Feb. 21, 1989.

* cited by examiner

NICOTINIC ACID COMPOSITIONS FOR TREATING HYPERLIPIDEMIA AND RELATED METHODS THEREFOR

RELATED PATENT APPLICATIONS

This application is a continuation of prior U.S. patent application Ser. No. 09/478,325, filed Jan. 6, 2000, now abandoned; which is a continuation of U.S. patent application Ser. No. 08/814,974, filed Mar. 6, 1997, now U.S. Pat. No. 6,129,930; which is a continuation-in-part of U.S. patent application Ser. No. 08/368,378, filed Jan. 14, 1995, now U.S. Pat. No. 6,080,428; which is a continuation-in-part of U.S. patent application Ser. No. 08/124,392, filed Sep. 20, 1993, now abandoned.

FIELD OF THE INVENTION

This invention generally relates to compositions of nicotinic acid useful for treating hyperlipidemia and methods of treating hyperlipidemia employing such compositions. More particularly, the present invention employs a composition of nicotinic acid, derivatives and mixtures thereof, and a swelling agent to form a time release sustaining composition for nocturnal or evening dosing. Specifically, the present invention employs a composition of nicotinic acid and hydroxypropyl methylcellulose to treat hyperlipidemia in a once per day oral dosage form given during the evening hours.

BACKGROUND

Nicotinic acid has been used for many years in the treatment of hyperlipidemia. This compound has long been known to exhibit the beneficial effects of reducing total cholesterol, low density lipoproteins or "LDL cholesterol", triglycerides and apolipoprotein a (Lp(a)) in the human body, while increasing desirable high density lipoproteins or "HDL cholesterol".

Nicotinic acid has normally been administered three times per day after meals. This dosing regimen is known to provide a very beneficial effect on blood lipids as discussed in Knopp et al; "Contrasting Effects of Unmodified and Time-Release Forms of Niacin on Lipoproteins in Hyperlipidemic Subjects: Clues to Mechanism of Action of Niacin"; Metabolism 34/7, 1985, page 647. The chief advantage of this profile is the ability of nicotinic acid to decrease total cholesterol, LDL cholesterol, triglycerides and Lp(a) while increasing HDL particles. While such a regimen does produce beneficial effects, cutaneous flushing and the like still often occurs in the hyperlipidemics to whom the compound is administered.

In order to avoid or reduce the cutaneous flushing, a number of materials have been suggested for administration with an effective antihyperlipidemic amount of nicotinic acid, including guar gun in U.S. Pat. No. 4,965,252, and mineral salts as disclosed in U.S. Pat. No. 5,023,245; or inorganic magnesium salts as reported in U.S. Pat. No. 4,911,917. These materials have been reported to avoid or reduce the cutaneous flushing side effect commonly associated with nicotinic acid treatment.

Another method of avoiding or reducing the side effects associated with immediate release niacin is the use of sustained release formulations. Sustained release formulations are designed to slowly release the compound from the tablet or capsule. The slow drug release reduces and prolongs blood levels of drug and thus minimizes the side effects. Sustained release formulations of niacin have been developed, such as Nicobid™ capsules (Rhone-Poulenc Rorer), Endur-acin™ (Innovite Corporation) and U.S. Pat. No. 5,126,145 which describes a sustained release niacin formulation containing two different types of hydroxypropyl methylcellulose and a hydrophobic component.

Studies in hyperlipidemic patients have been conducted with a number of sustained release niacin products. These studies have demonstrated that the sustained release products do not have the same advantageous lipid altering effects as immediate release niacin, and in fact often have a worse side effect profile compared to the immediate release product. The major disadvantage of the sustained release formulations, as can be seen in Knopp et al., 1985, is the significantly lower reduction in triglycerides (−2% for the sustained release versus −38% for the immediate release) and lower increase in HDL cholesterol, represented as HDL particles which are known by the art to be most beneficial, (−5 % for the sustained release versus +37% for the inmediate release).

Additionally, sustained release niacin formulations have been noted as causing greater incidences of liver toxicity as described in Henken et al (Am J Med 91:1991 1991) and Dalton et al (Am J Med 93: 102 1992). There is also great concern regarding the potential of these formulations in disrupting glucose metabolism and uric acid levels.

In a recent edition of the Journal of the American Medical Association (JAMA), an article appeared which presented research results investigating the liver toxicity problems associated with a sustained release form of nicotinic acid. "A Comparison of the Efficacy and Toxic Effects of Sustained- vs. Immediate-Release Niacin in Hypercholesterolemic Patients", McKenney et al., JAMA, Vol. 271, No. 9, Mar. 2, 1994, page 672. The article presented a study of twenty-three patients. Of that number, 12 or 52 percent were forced to withdraw because liver function tests (LFTs) increased indicating potential liver damage. The conclusion of the authors of that article was that the sustained release form of niacin "should be restricted from use."

A similar conclusion was reached in an article authored by representatives of the Food and Drug Administration and entitled "Hepatic Toxicity of Unmodified and Time-Release Preparations of Niacin", Rader, et al., THE AMERICAN JOURNAL OF MEDICINE, Vol. 92, Jan. 1992, page 77. Because of these studies and similar conclusions drawn by other health care professionals, the sustained release forms of niacin have experienced limited utilization.

Therefore, it can be seen from the scientific literature that there is a need for development of a sustained release niacin formulation and a method of delivering said formulation which would provide hyperlipidemic patients with "balanced lipid alteration", i.e. reductions in total cholesterol, LDL cholesterol, triglycerides and Lp(a) as well as increases in HDL particles, with an acceptable safety profile, especially as regards liver toxicity and effects on glucose metabolism and uric acid levels.

SUMMARY OF THE INVENTION

In brief, the present invention alleviates and overcomes certain of the above-identified problems and shortcomings of the present state of nicotinic acid therapy through the discovery of novel nicotinic acid formulations and methods of treatment.

It is therefore, an object of the present invention to provide a composition of nicotinic acid or any compound which is metabolized by the body to form nicotinic acid for treating hyperlipidemia.

It is another object of the present invention to provide a composition as above, which has a time release sustaining characteristic.

It is yet another object of the present invention to provide a method for employing a composition as above, for treating hyperlipidemia, which results in little or no liver damage.

At least one or more of the foregoing objects, together with the advantages thereof over the known art relating to the treatment of hyperlipidemia, which shall become apparent from the specification which follows, are accomplished by the invention as hereinafter described and claimed.

In general the present invention provides an improved antihyperlipidemia composition of the oral type employing an effective antihyperlipidemic amount of nicotinic acid, wherein the improvement comprises compounding the nicotinic acid with from about 5% to about 50% parts by weight of hydroxypropyl methylcellulose per hundred parts by weight of tablet or formulation.

The present invention also provides an orally administered antihyperlipidemia composition which comprises from about 30% to about 90% parts by weight of nicotinic acid; and, from about 5% to about 50% parts by weight of hydroxypropyl methylcellulose.

The present invention also includes a method of treating hyperlipidemia in a hyperlipidemic. The method comprises the steps of forming a composition which comprises an effective antihyperlipidemic amount of nicotinic acid and an amount of excipients to provide sustained release of drug. The method also includes the step of orally administering the composition to the hyperlipidemic nocturnally.

A method of treating hyperlipidemia in a hyperlipidemic according to the invention, comprises dosing the hyperlipidemic with an effective antihyperlipidemic amount of nicotinic acid or compound metabolized to nicotinic acid by the body. The dose is given once per day in the evening or at night, combined with a pharmaceutically acceptable carrier to produce a significant reduction in total and LDL cholesterol as well as a significant reduction in triglycerides and Lp(a), with a significant increase in HDL cholesterol.

The above features and advantages of the present invention will be better understood with reference to the following detailed description and examples. It should also be understood that the particular methods and formulations illustrating the present invention are exemplary only and not to be regarded as limitations of the present invention.

DETAILED DESCRIPTION OF THE INVENTION

By way of illustrating and providing a more complete appreciation of the present invention and many of the attendant advantages thereof, the following detailed description and examples are given concerning the novel methods and formulations.

The present invention employs nicotinic acid or a compound other than nicotinic acid itself which the body metabolizes into nicotinic acid, thus producing the same effect as described herein. The other compounds specifically include, but are not limited to the following: nicotinyl alcohol tartrate, d-glucitol hexanicotinate, aluminum nicotinate, niceritrol and d,1alpha-tocopheryl nicotinate. Each such compound will be collectively referred to hereinbelow by "nicotinic acid."

As stated hereinabove, nicotinic acid has been employed in the past for the treatment of hyperlipidemia, which condition is characterized by the presence of excess fats such as cholesterol and triglycerides, in the blood stream. According to the present invention, a sustained release composition of nicotinic acid is prepared as an example. By "sustained release" it is understood to mean a composition which when orally administered to a patient to be treated, the active ingredient will be released for absorption into the blood stream over a period of time. The release rate of nicotinic acid or the compound metabolized to nicotinic acid by the body is about 2% per hour to about 25% per hour. For example, it is preferred that in a dosage of about 1500 milligrams (hereinafter "mgs") of nicotinic acid, approximately 100 percent of the nicotinic acid will be released to the blood stream in about 4 to about 24 hours.

The specific sustained release composition according to the present invention employs an effective antihyperlipidemic amount of nicotinic acid. By "effective antihyperlipidemic amount" it is understood to mean an amount which when orally administered to a patient to be treated, will have a beneficial effect upon the physiology of the patient, to include at least some lowering of total cholesterol, LDL cholesterol, triglycerides and Lp(a) and at least some increase in HDL cholesterol in the patient's blood stream. An exemplary effective antihyperlipidemic amount of nicotinic acid would be from about 250 mgs to about 3000 mgs of nicotinic acid to be administered according to the invention as will be more fully described hereinbelow. According to another aspect of the present invention, from about 100 mgs to about 500 mgs of nicotinyl alcohol tartrate per dosage unit of the present formulation is an exemplary effective amount to be administered. The amount of nicotinic acid or compound other than nicotinic acid which metabolizes into nicotinic acid, which is an effective hyperlipidemic amount, will vary dependent upon a number of variables, including the physiological needs of the patient to be treated.

Preferably, there is also included in the sustained release composition according to the present invention, a swelling agent which is compounded with the nicotinic acid, such that when the composition is orally administered to the patient, the swelling agent will swell over time in the patient's gastrointestinal tract, and release the active nicotinic acid, or a compound which produces nicotinic acid into the gastrointestinal system for absorption into the blood stream, over a period of time. As is known in the art, such swelling agents and amounts thereof, may be preselected in order to control the time release of the active ingredient. Such swelling agents include, but are not limited to, polymers such as sodium carboxymethylcellulose and ethylcellulose and waxes such as bees wax and natural materials such as gums and gelatins or mixtures of any of the above. Because the amount of the swelling agent will vary depending upon the nature of the agent, the time release needs of the patient and the like, it is preferred to employ amounts of the agent which will accomplish the objects of the invention.

An exemplary and preferred swelling agent is hydroxypropyl methylcellulose, in an amount ranging from about 5% to about 50% parts by weight per 100 parts by weight of tablet or formulation. The preferred example will ensure a sustained time release over a period of approximately 4-24 hours as demonstrated by in vitro dissolution techniques known to the art.

A binder may also be employed in the present compositions. While any known binding material is useful in the present invention, it is preferred to employ a material such as one or more of a group of polymers having the repeating unit of 1-ethenyl-2-pyrrolidinone. These polymers generally have molecular weights of between about. 10,000 and 700,000, and are also known as "povidone".

Amounts of the binder material will of course, vary depending upon the nature of the binder and the amount of other ingredients of the composition. An exemplary amount of povidone in the present compositions would be from about 1% to about 5% by weight of povidone per 100 parts by weight of the total formulation.

Processing aids such as lubricants, including stearic acid, may also be employed, as is known in the art. An exemplary amount of stearic acid in the present compositions would be from about 0.5% to about 2.0% by weight per 100 parts by weight of tablet or formulation.

Examples of various embodiments of the present invention will now be further illustrated with reference to the following examples.

General Experimental

An embodiment of the invention includes a method for treating hyperlipidemia in a hyperlipidemic, the method comprising the step of dosing the hyperlipidemic once a day, in the evening or at night, with at least one sustained release solid oral dosage form comprising (i) about 375, about 500, about 750 or about 1000 mgs of nicotinic acid; (ii) about 5% to about 50% by weight of hydroxypropyl methylcellulose; (iii) about 1% to about 5% by weight of povidone; and (iv) about 0.5% to about 2.0% by weight of stearic acid, wherein the hyperlipidemic's total cholesterol, LDL cholesterol, triglycerides and Lp(a) are reduced and the hyperlipidemic's HDL cholesterol is increased, and wherein the total amount of nicotinic acid dosed to a hyperlipidemic in a day is between about 1000 to about 3000 mgs.

In order to demonstrate the effectiveness of the compositions and method of the present invention over known antihyperlipidemia compositions and methods heretofore known in the art, a number of substantially identical composition were prepared according to the disclosure hereinabove. The composition ingredients and amounts are listed in TABLE IA hereinbelow.

TABLE IA

Test Tablet Composition

| Ingredient | 375 mg. | 500 mg | 750 mg |
|---|---|---|---|
| Nicotinic Acid | 375.0 | 500.0 | 750.0 |
| Hyroxypropyl methylcellulose | 188.7 | 203.0 | 204.7 |
| Povidone | 12.9 | 17.2 | 25.9 |
| Stearic Acid | 5.8 | 7.3 | 9.9 |
| TOTAL | 582.4 mg | 727.5 mg | 990.5 mg |

The ingredients were compounded together to form a tablet. More specifically, Niaspan® once-daily tablets in accordance with the present invention utilize a hydrophilic matrix controlled drug delivery system. This is a dynamic system composed of polymer wetting, polymer hydration and polymer disintegration/dissolution. The mechanism by which drug release is controlled depends on, for example, initial polymer wetting, expansion of the gel layer, tablet erosion and niacin solubility. After initial wetting, the hydrophilic polymer starts to partially hydrate, forming a gel layer. As water permeates into the tablet increasing the thickness of the gel layer, drug diffuses out of the gel layer. As the outer layer of the tablet becomes fully hydrated it erodes. It is believed that this erosion results in additional drug release. The controlled release from this matrix delivery system can be modified depending on the type and molecular weight of hydrophilic polymer used.

A Niaspan® formulation consists of Niacin, Methocel® E10M Premium, Povidone K90 and Hystrene 5016 (stearic acid). Methocel®E10M Premium is utilized as a controlled-release agent in the Niaspan® formulation. Methocel is a partly O-methylated and O-(2-hydroxypropylated) cellulose and is available in several grades which vary in terms of viscosity and degree of substitution. Methocel is manufactured by Dow Chemical.

Povidone K90 is employed as a granulating/binding agent in a Niaspan® formulation. Povidone is a synthetic polymer consisting of linear 1-vinyl-2-pyrrolidone groups, the degree of polymerization of which results in polymers of various molecular weights, or as indicated above. It is characterized by its viscosity in aqueous solution, relative to that of water, expressed as a K-value, ranging from 10-120. Povidone K90 has an approximate molecular weight of 1,000,000. Povidone is a hygroscopic, water soluble material. Povidone K90 present in a Niaspan® formulation is manufactured by ISP (International Specialty Products). Hystrene 5016 is utilized as an external lubricant in the Niaspan® formulation. Hystrene 5016 is a mixture of stearic acid and palmitic acid. The content of stearic acid is not less than about 40.0% and the sum of the two acids is not less than about 90.0%. Hystrene 5016 is manufactured by Witco. Refer to Table IB for Niaspan® formulation details.

Qualitatively, the four tablet strength formulations are identical. The major component of each formulation is a granulated mixture of Niacin, Methocel E10M and Povidone K90. The granulation process improves compression properties.

TABLE IB

Niaspan Tablet Formulations

| Niaspon ® Product | 375 mg Tablets | 500 mg Tablets | 750 mg Tablets | 1000 mg Tablets |
|---|---|---|---|---|
| Formulation, %/Tablet | | | | |
| Niacin | 64.4 | 70.5 | 77.4 | 83.1 |
| Methocel E10M Premium (Intragranular) | 7.4 | 8.1 | 8.9 | 9.5 |
| Povidone K90 | 2.2 | 2.4 | 2.7 | 2.9 |
| Methocel E10M Premium (Extragranular) | 25.0 | 18.0 | 10.0 | 3.5 |
| Hystrene 5016 (Stearic Acid) | 1.0 | 1.0 | 1.0 | 1.0 |
| Tablet weight, mg | 582.5 | 709.5 | 968.6 | 1203.6 |

Niaspan® formulations are presented in white caplet shape tablets. Caplet dimensions differ with respect to product strength. The 375 mg and 500 mg Niaspan®tablets are compressed with tooling measuring approximately 0.687" in length×0.281" by width. The length and width of the 750 mg and 1000 mg tooling measures approximately 0.750"×0.320". Target tablet weight and hardness dictate thickness across the four Niaspan® products. The production of the Niaspan® tablets will now be described generally as set forth below.

Niaspan Granulation Process Flow Chart

| Raw Materials | Process Flow | Equipment |
|---|---|---|
| Niacin<br>Povidone K90<br>Methocel E10M<br>(Intragranular)<br>Purified Water | Granulate<br><br><br><br>↓ | High shear granulator<br>(Littleford FM130) |

-continued

| Raw Materials | Process Flow | Equipment |
| --- | --- | --- |
| | Dry | Fluid bed drier (Glatt fluid bed drier) |
| | ↓ | |
| | Parcel size reduction | Mill (Kemutec Betagrind) |

Niaspan® Granulation Process Description

Niaspan® granulation raw materials are dispensed and granulated in a high shear granulator. The wet granules are sieved into a fluid bed drier and are dried. When the drying process is complete, the granules are milled. Milling ensures uniform particle size distribution throughout the Niaspan® granulation.

Niaspan® Tablet Process Flow Chart

| Raw Materials | Process Flow | Equipment |
| --- | --- | --- |
| Methocel E10M (Extragranular Hystrene 5016 (Stearic acid) | Niaspan Tablet Blend Blend Milled Niaspan ® granules with extragranular Methocel E10M and Hystrene 5016 | Blender (Patterson-Kelley V- Blender) |
| | ↓ | |
| | Niaspan ® Tablet Manufacture Compress Niaspan ® Tablet Blend | Rotary tablet press |

Niaspan® Tablet Process Description

A Niaspan® tablet blend is manufactured by blending the Niaspan® granulation, extragranular Methocel E10M and Hystrene 5016. The quantities of each Niaspan® tablet blend component will depend on the particular Niaspan® dose being manufactured (refer to Table IB). A Niaspan® tablet blend is compressed to form Niaspan® tablets. Niaspan® tablet physical properties will vary depending on the particular Niaspan® dose being manufactured.

Production of Niaspan® tablets will now be discussed in greater detail. The initial stage of manufacturing is the same for all four tablet strengths of Niaspan® (375, 500, 750, and 1000 mg). One batch of Niaspan® granulation is comprised of four individual 40.0 kg units of granulation which are processed separately, but under like conditions. The four individual granulations are sampled and tested individually and subsequently released for blending. The base granulation is not strength specific and may be used to manufacture any tablet strength of Niaspan® .

The ingredients in the base granulation are set forth in Table IC below:

TABLE IC

| Component | Function | Quantity per kilogram granulation (kg) | % per kilogram granula- tion (%) | Quantity per 160.00 kg batch (kg) |
| --- | --- | --- | --- | --- |
| Niacin, USP | Drug Substance | 0.87 | 87.00 | 139.20 |
| Povidone, USP | Binder | 0.03 | 3.00 | 4.80 |
| Methocel USP, E10M Premium CR Grade | Controlled- Release Agent | 0.10 | 10.00 | 16.00 |

TABLE IC-continued

| Component | Function | Quantity per kilogram granulation (kg) | % per kilogram granula- tion (%) | Quantity per 160.00 kg batch (kg) |
| --- | --- | --- | --- | --- |
| Purified Water, USP* | Granulation Reagent | 0.00* | 0.00* | 48.00 |
| Total | | | | 160.00 |

*Purified Water, USP is used as a granulation reagent and does not appear in the finished granulation.

Raw materials are quantatively dispensed into appropriately labeled double polyethylene-lined containers using calibrated scales. Purified Water, USP is dispensed into an appropriate vessel from which it is later pumped during the wet-massing operation.

A Littleford FM130 granulator is charged with approximately one half of the Niacin, USP required for the process unit (~17.4 kg) followed by about 4.00 kg of Methocel, USP E10M Premium CR Grade; about 1.20 kg of Povidone, USP; and the balance of the Niacin, SP (~17.40 kg). The powder bed is dry mixed in the Littleford FM130 granulator, with choppers on, for approximately 1 minute. At the completion of the 1-minute premix cycle, about 12.0±0.05 kg of Purified Water, USP are sprayed onto the powder bed at a rate of about 2.40±0.24 kg/minute. Immediately following the addition of the Purified Water, USP, the unit is granulated for about 5 minutes.

The granulated unit is discharged into double polyethylenelined containers and then manually loaded into a Glatt bowl while being passed through a #4 mesh screen, the Glatt bowl is loaded into a Glatt TFO-60 fluid-bed drier with an inlet air temperature setting of about 70° C.±5° C. The unit is dried until a moisture level of ≦1.0% is obtained as determined using a Computrac® Moisture Analyzer, model MA5A. The dried granulation is discharged into appropriately labeled, double polyethylene-lined drums and reconciled.

The dried and reconciled granulation is passed through a Kemutec BetaGrind mill equipped with a 1.5 mm screen and running at approximately 1500 RPM. The milled granulation is collected into appropriately labeled, double polyethylene-lined drums and reconciled. The milled granulation is sampled and tested by Quality Control and released prior to further processing.

The released granulation units are charged to a Patterson-Kelley 20 ft³ V-blender after which they are blended together for about 10±1 minutes and then discharged to appropriately labeled, double polyethylene-lined containers.

As stated above, Niaspan® tablets are formulated from a common granulation which is blended with appropriate quantities of Methocel, USP E10M Premium CR Grade and Stearic Acid, NF to achieve the final dosage formulation. Tables IA and IB describe the formulation for each Niaspan® tablet strength, 375 mg, 500 mg, 750 mg, and 1000 mg, respectively.

Two study groups consisting of eleven and fourteen patients each were formed. Blood samples were taken from the patients, and tested for total cholesterol, LDL cholesterol, triglycerides and HDL cholesterol to establish baseline levels from which fluctuations in these lipids could be compared. The patients were then placed upon a regimen of the above discussed tablets, totalling approximately 1500 mg of nicotinic acid, once per day before going to bed. After eight weeks of this regimen, the patients were again tested for lipid profiles. The results of the tests conducted at eight weeks, showing the changes in the lipid profiles as a percentage change from the baseline, are reported in the table hereinbelow. Positive numbers reflect percentage increases and negative numbers reflect percentage decreases in this table.

TABLE II

Patient Study Lipid Profile Data

| Pt. No. | Total-C | LDL-C | Apo B | Trigs | HDL-C | HDL$_2$-C | Lp(a) |
|---|---|---|---|---|---|---|---|
| GROUP A | | | | | | | |
| 1 | −11.9 | −17.9 | NA | −17.3 | 22.0 | NA | NA |
| 2 | −9.4 | −33.1 | NA | −28.7 | 65.4 | NA | NA |
| 3 | −20.6 | −13.1 | NA | −43.7 | −6.3 | NA | NA |
| 4 | −7 | −15.9 | NA | 61.6 | 3.8 | NA | NA |
| 5 | −20.3 | −24.3 | NA | −28.8 | 11.1 | NA | NA |
| 6 | −15.6 | −31.2 | NA | −42.0 | 51.6 | NA | NA |
| 7 | −27.6 | −36.8 | NA | −39.4 | 12.5 | NA | NA |
| 8 | −10.6 | −13.8 | NA | −42.4 | 18.8 | NA | NA |
| 9 | 4.5 | 1.1 | NA | 7.2 | 9.2 | NA | NA |
| 10 | −.7 | −5.5 | NA | −2.7 | 22.9 | NA | NA |
| 11 | −15.4 | −.4 | NA | −67.6 | 50.0 | NA | NA |
| Mean | −12.3 | −17.4 | NA | −22.1 | 23.7 | NA | NA |
| p-Value | 0.0004 | 0.0001 | | 0.0371 | 0.0068 | | |
| GROUP B | | | | | | | |
| 1 | −19.2 | −27.1 | −24.4 | −33.4 | 20.0 | 22.3 | 8.1 |
| 2 | −32.2 | −35.7 | −28.0 | −60.4 | 4.3 | 3.2 | −25.3 |
| 3 | −17.3 | −28.4 | −35.6 | −41.6 | 34.6 | 38.6 | 0 |
| 4 | −19.9 | −24.6 | −15.1 | −20.8 | 9.6 | 16.1 | −27.0 |
| 5 | −3.3 | −2.1 | −29.4 | −41.1 | 5.8 | −2.3 | −22.4 |
| 6 | PATIENT WITHDREW FROM STUDY | | | | | | |
| 7 | −23.1 | −32.6 | −40.8 | −58.6 | 49.2 | 62.1 | −14.3 |
| 8 | 24.8 | 34.0 | −28.4 | 5.5 | 6.5 | 0 | NA |
| 9 | 10.1 | 12.0 | −16.8 | −11.6 | 20.7 | −11.6 | 40.6 |
| 10 | −2.9 | −7.7 | −28.0 | −59.0 | 53.1 | 70.5 | −41.2 |
| 11 | −10.5 | −18.8 | −31.3 | −53.4 | 31.8 | 34.2 | NA |
| 12 | −20.0 | −30.8 | −30.4 | 11.7 | 21.1 | 25.0 | −28.4 |
| 13 | −9.4 | −16.6 | −17.5 | −46.9 | 52.3 | 51.9 | −17.6 |
| 14 | 17.4 | 16.8 | −22.6 | −17.5 | 51.3 | 5.4 | 38.5 |
| Mean | −8.1 | −12.4 | −26.8 | −32.9 | 27.7 | 24.3 | −6.9 |
| p-Value | 0.0002 | <0.0001 | 0.0001 | <0.001 | <0.0001 | 0.0002 | <0.0188 |
| Combined | −8.7 | 13.3 | Gp B | −26.1 | 25.3 | Gp B | Gp B |
| p-Value | 0.0002 | <0.0001 | only | <0.0001 | <0.0001 | only | only |

The data reported in TABLE II shows that the LDL levels in the Group A patients had a mean decrease of −13.9% and triglyceride decrease of −18.9% HDL, cholesterol levels, the beneficial cholesterol, were raised by 23.0% in this Group. Similar results were obtained with the Group B patients. These studies demonstrate that dosing the sustained release formulation during the evening hours or at night provides reductions in LDL cholesterol levels equal to immediate release niacin on a milligram per milligram basis, but superior reductions in triglyceride reductions when compared to sustained release formulations dosed during daytime hours on a milligram per milligram basis. Additionally, the increases in HDL cholesterol obtained from dosing the sustained release formulation during the evening or at night were +23.0% for one group and +25.3% for the other group. Dosing during the evening therefore provides reduction in LDL cholesterol plus significant decreases in triglycerides and increases in HDL cholesterol with once-a-day dosing.

Groups A and B were also tested for liver enzymes (AST, ALT and Alkaline Phosphatase), uric acid and fasting glucose levels at the start of the study described hereinabove (to form a baseline) and at two, four and eight week intervals. The results of these tests are listed in TABLES III-VII hereinbelow.

TABLE III

THE EFFECT OF NIASPAN ® THERAPY
ON AST (SGOT) LEVELS (U/L)
(1500 mgs dosed once-a-day at night)
(n = 28)

| | Weeks of Therapy With NIASPAN ™ | | | | Reference |
|---|---|---|---|---|---|
| Pt # | Baseline | 2 Wks. | 4 Wks. | 8 Wks. | Range |
| GROUP A | | | | | |
| 1 | 28 | 29 | 25 | 24 | 0-50 |
| 2 | 24 | 25 | 24 | 26 | 0-50 |
| 3 | 17 | 18 | 22 | 21 | 0-50 |
| 4 | 14 | 16 | 15 | 17 | 0-50 |
| 5 | 22 | NA | 32 | 52 | 0-50 |
| 6 | 21 | 17 | 17 | 14 | 0-50 |
| 7 | 17 | 17 | 14 | 18 | 0-50 |
| 8 | 20 | 21 | 22 | 22 | 0-50 |
| 9 | 16 | 16 | 17 | 20 | 0-50 |
| 10 | 18 | 21 | 21 | 25 | 0-50 |
| 11 | 21 | 21 | 22 | 21 | 0-50 |
| GROUP B | | | | | |
| 1 | 23 | 25 | 38 | 33 | 0-50 |
| 2 | 20 | 20 | 21 | 21 | 0-50 |
| 3 | 15 | 20 | 18 | 19 | 0-50 |

TABLE III-continued

THE EFFECT OF NIASPAN ® THERAPY
ON AST (SGOT) LEVELS (U/L)
(1500 mgs dosed once-a-day at night)
(n = 28)

| Pt # | Baseline | 2 Wks. | 4 Wks. | 8 Wks. | Reference Range |
|---|---|---|---|---|---|
| 4 | 25 | 22 | 25 | 26 | 0-50 |
| 5 | 23 | 21 | 17 | 18 | 0-50 |
| 6 | PATIENT WITHDREW DUE TO FLUSHING | | | | |
| 7 | 21 | 18 | 18 | 19 | 0-50 |
| 8 | 18 | 19 | 18 | 19 | 0-50 |
| 9 | 15 | 16 | 18 | 15 | 0-50 |
| 10 | 16 | 15 | 19 | 28 | 0-50 |
| 11 | 20 | 22 | 24 | 28 | 0-50 |
| 12 | 23 | 25 | 28 | 22 | 0-50 |
| 13 | 20 | 15 | 20 | 19 | 0-50 |
| 14 | 18 | 25 | 20 | 18 | 0-50 |
| Combined Mean | 19.8 | 20.4 | 20.8 | 21.1 | |
| Change From Baseline | | +3.0% | +5.1% | +6.6% | |

Level of Significance: p = 0.4141

TABLE IV

THE EFFECT OF NIASPAN ® THERAPY ON
ALT (SGPT) LEVELS (U/L)
(1500 mgs dosed once-a-day at night)
(n = 28)

| Pt # | Baseline | 2 Wks. | 4 Wks. | 8 Wks. | Reference Range |
|---|---|---|---|---|---|
| GROUP A | | | | | |
| 1 | 32 | 28 | 39 | 30 | 0-55 |
| 2 | 24 | 25 | 23 | 26 | 0-55 |
| 3 | 18 | 23 | 30 | 30 | 0-55 |
| 4 | 7 | 13 | 14 | 14 | 0-55 |
| 5 | 14 | NA | 43 | 46 | 0-55 |
| 6 | 22 | 11 | 14 | 10 | 0-55 |
| 7 | 9 | 7 | 11 | 7 | 0-55 |
| 8 | 16 | 18 | 23 | 21 | 0-55 |
| 9 | 14 | 17 | 20 | 14 | 0-55 |
| 10 | 14 | 15 | 17 | 19 | 0-55 |
| 11 | 18 | 18 | 20 | 16 | 0-55 |
| GROUP B | | | | | |
| 1 | 16 | 17 | 27 | 29 | 0-55 |
| 2 | 16 | 14 | 15 | 22 | 0-55 |
| 3 | 13 | 21 | 13 | 16 | 0-55 |
| 4 | 23 | 20 | 26 | 17 | 0-55 |
| 5 | 21 | 23 | 17 | 15 | 0-55 |
| 6 | PATIENT WITHDREW DUE TO FLUSHING | | | | |
| 7 | 21 | 16 | 18 | 21 | 0-55 |
| 8 | 18 | 20 | 17 | 18 | 0-55 |
| 9 | 11 | 5 | 11 | 8 | 0-55 |
| 10 | 8 | 10 | 14 | 17 | 0-55 |
| 11 | 17 | 12 | 18 | 16 | 0-55 |
| 12 | 14 | 18 | 20 | 16 | 0-55 |
| 13 | 14 | NA | 11 | 10 | 0-55 |
| 14 | 23 | 23 | 19 | 19 | 0-55 |
| Combined Mean | 17.7 | 17.5 | 19.3 | 18.2 | |
| Change From Baseline | | −1.1% | 9.0% | +2.8% | |

Level of Significance: p = 0.3424

TABLE V

THE EFFECT OF NIASPAN THERAPY ON ALKALINE
PHOSPHATASE LEVELS (U/L)
(1500 mgs dosed once-a-day at night)
(n = 28)

| Pt # | Baseline | 2 Wks. | 4 Wks. | 8 Wks. | Reference Range |
|---|---|---|---|---|---|
| GROUP A | | | | | |
| 1 | 52 | 56 | 57 | 55 | 20-140 |
| 2 | 103 | 100 | 89 | 102 | 20-140 |
| 3 | 54 | 45 | 53 | 51 | 20-140 |
| 4 | 70 | 68 | 71 | 91 | 20-140 |
| 5 | 77 | NA | 74 | 81 | 20-140 |
| 6 | 55 | 48 | 49 | 51 | 20-140 |
| 7 | 72 | 71 | 79 | 75 | 20-140 |
| 8 | 55 | 49 | 47 | 50 | 20-140 |
| 9 | 53 | 55 | 56 | 45 | 20-140 |
| 10 | 74 | 73 | 75 | 75 | 20-140 |
| 11 | 18 | 18 | 20 | 16 | 20-140 |
| GROUP B | | | | | |
| 1 | 73 | 67 | 89 | 95 | 20-140 |
| 2 | 82 | 64 | 72 | 71 | 20-140 |
| 3 | 73 | 69 | 72 | 82 | 20-140 |
| 4 | 37 | 36 | 37 | 38 | 20-140 |
| 5 | 65 | 53 | 54 | 61 | 20-140 |
| 6 | PATIENT WITHDREW DUE TO FLUSHING | | | | |
| 7 | 64 | 58 | 58 | 58 | 20-140 |
| 8 | 79 | 78 | 65 | 73 | 20-140 |
| 9 | 94 | 92 | 103 | 93 | 20-140 |
| 10 | 69 | 67 | 70 | 65 | 20-140 |
| 11 | 59 | 67 | 63 | 72 | 20-140 |
| 12 | 65 | 59 | 59 | 63 | 20-140 |
| 13 | 64 | 68 | 66 | 64 | 20-140 |
| 14 | 72 | 61 | 59 | 64 | 20-140 |
| Combined Mean | 66.5 | 61.5 | 63.3 | 65.8 | |
| Change From Baseline | | −6.1% | −3.4% | +0.005% | |

Level of Significance: p = 0.0236

TABLE VI

THE EFFECT OF NIASPAN THERAPY ON
URIC ACID LEVELS (mg/dL)
(1500 mgs dosed once-a-day at night)
(n = 28)

| Pt # | Baseline | 2 Wks. | 4 Wks. | 8 Wks. | Reference Range |
|---|---|---|---|---|---|
| GROUP A | | | | | |
| 1 | 5.2 | 5.0 | 4.8 | 4.3 | 4.0-8.5 |
| 2 | 4.0 | 4.6 | 4.5 | 6.2 | 2.5-7.5 |
| 3 | 6.3 | 7.0 | 6.5 | 6.2 | 4.0-8.5 |
| 4 | 3.1 | 4.6 | 4.2 | 3.8 | 2.5-7.5 |
| 5 | 3.4 | NA | 3.3 | 4.2 | 2.5-7.5 |
| 6 | 6.6 | 5.5 | 5.6 | 4.7 | 4.0-8.5 |
| 7 | 3.8 | 4.5 | 4.3 | 4.9 | 2.5-7.5 |
| 8 | 4.4 | 3.8 | 5.1 | 4.5 | 2.5-7.5 |
| 9 | 3.9 | 4.5 | 4.6 | 3.5 | 2.5-7.5 |
| 10 | 2.6 | 2.9 | 2.8 | 2.7 | 2.5-7.5 |
| 11 | 4.7 | 5.5 | 5.2 | 5.3 | 2.5-7.5 |
| GROUP B | | | | | |
| 1 | 3.7 | 4.2 | 4.7 | 3.5 | 2.5-7.5 |
| 2 | 2.8 | 3.5 | 3.6 | 2.3 | 4.0-8.5 |
| 3 | 4.2 | 5.3 | 5.5 | 5.3 | 2.5-7.5 |
| 4 | 4.7 | 3.9 | 5.1 | 3.6 | 4.0-8.5 |
| 5 | 3.7 | 4.1 | 4.1 | 3.8 | 2.5-7.5 |

TABLE VI-continued

THE EFFECT OF NIASPAN THERAPY ON
URIC ACID LEVELS (mg/dL)
(1500 mgs dosed once-a-day at night)
(n = 28)

| Pt # | Weeks Of Therapy With NIASPAN | | | Reference |
|---|---|---|---|---|
| | Baseline | 2 Wks. | 4 Wks. | 8 Wks. | Range |
| 6 | PATIENT WITHDREW DUE TO FLUSHING | | | |
| 7 | 5.8 | 6.6 | 6.6 | 6.8 | 2.5-7.5 |
| 8 | 4.7 | 4.3 | 5.4 | 5.6 | 2.5-7.5 |
| 9 | 3.7 | 4.6 | 5.1 | 3.8 | 2.5-7.5 |
| 10 | 4.2 | 5.0 | 4.4 | 8.5 | 2.5-7.5 |
| 11 | 1.9 | 3.0 | 2.8 | 5.0 | 2.5-7.5 |
| 12 | 5.6 | 5.4 | 6.2 | 5.6 | 4.0-8.5 |
| 13 | 4.2 | 4.6 | 4.6 | 5.3 | 2.5-7.5 |
| 14 | 5.5 | 5.4 | 6.1 | 5.3 | 2.5-7.5 |
| Combined Mean | 4.54 | 4.82 | 4.92 | 4.86 | *p = 0.3450 |
| Change From Baseline | | +6.2% | +8.4% | +7.0% | |

*Level of Significance: p = 0.3450

TABLE VII

THE EFFECT OF NIASPAN THERAPY ON FASTING
GLUCOSE LEVELS (mg/dL)
(1500 mgs dosed once-a-day at night)
(n = 28)

| Pt # | Weeks Of Therapy With NIASPAN ® | | | Reference |
|---|---|---|---|---|
| | Baseline | 2 Wks. | 4 Wks. | 8 Wks. | Range |
| GROUP A | | | | | |
| 1 | 114 | 122 | 123 | 110 | 70-115 |
| 2 | 101 | 105 | 107 | 101 | 80-125 |
| 3 | 99 | 98 | 109 | 103 | 70-115 |
| 4 | 100 | 118 | 94 | 94 | 80-125 |
| 5 | 89 | NA | 82 | 103 | 80-125 |
| 6 | 97 | 103 | 94 | 107 | 70-115 |
| 7 | 85 | 107 | 100 | 94 | 80-125 |
| 8 | 98 | 107 | 103 | 101 | 80-125 |
| 9 | 97 | 97 | 100 | 110 | 80-125 |
| 10 | 94 | 101 | 111 | 97 | 70-115 |
| 11 | 102 | 103 | 95 | 95 | 80-125 |
| GROUP B | | | | | |
| 1 | 101 | 97 | 83 | 99 | 70-115 |
| 2 | 90 | 95 | 96 | 89 | 80-125 |
| 3 | 96 | 98 | 95 | 97 | 70-115 |
| 4 | 116 | 139 | 113 | 125 | 80-125 |
| 5 | 88 | 92 | 91 | 95 | 70-115 |
| 6 | PATIENT WITHDREW DUE TO FLUSHING | | | |
| 7 | 106 | 114 | 118 | 117 | 70-115 |
| 8 | 95 | 106 | 106 | 108 | 70-115 |
| 9 | 81 | 92 | 84 | 92 | 70-115 |
| 10 | 108 | 117 | 122 | 105 | 70-115 |
| 11 | 85 | 106 | 106 | 108 | 70-115 |
| 12 | 92 | 89 | 101 | 86 | 80-125 |
| 13 | 99 | 105 | 94 | 100 | 70-125 |
| 14 | 100 | 108 | 84 | 107 | 70-125 |
| Combined Mean | 98.4 | 105.8 | 101.6 | 102.3 | |
| Change From Baseline | | +7.5% | +3.3% | +4.0% | |

Level of Significance: p = 0.0021

In order to provide a comparison between the state of the art prior to the present invention, and in order to quantify the magnitude of the improvement that the invention provides over the prior art, another study was conducted. This study included 240 patients dosed according to the present invention as described hereinabove. Compared to this group was the group of patients studied by McKenney et al., as reported hereinabove. The results of this study are reported in TABLE VIII hereinbelow.

TABLE VIII

A Comparison of Changes in Liver Function Tests

| | DOSE | | | | | | | TOTAL |
|---|---|---|---|---|---|---|---|---|
| | 0 | 500 | 1000 | 1500 | 2000 | 2500 | 3000 | |
| McKenney SR[b] Niacin | | | | | | | | |
| AST | 23.8 | 27.9 | 40.4 | 36.6 | 56.5 | na | 97.0 | |
| % | — | 117 | 170 | 154 | 237 | na | 408 | |
| Invention Dosage[c] | | | | | | | | |
| AST | 24.3 | na | 23.7 | 27.5 | 26.6 | 27.6 | 27.8 | |
| % | — | na | 98 | 113 | 109 | 114 | 114 | |
| McKenney SR Niacin | | | | | | | | |
| ALT | 25.6 | 29.5 | 36.3 | 39.0 | 59.1 | na | 100.0 | |
| % | — | 115 | 142 | 152 | 231 | na | 391 | |
| Invention Dosage | | | | | | | | |
| ALT | 21.4 | na | 18.7 | 22.6 | 21.3 | 22.4 | 21.8 | |
| % | — | na | 87 | 106 | 100 | 105 | 102 | |
| McKenney SR Niacin | | | | | | | | |
| ALK | 95 | 95 | 106 | 105 | 136 | na | 135 | |
| % | — | 100 | 112 | 111 | 143 | na | 142 | |
| Invention Dosage | | | | | | | | |
| ALK | 74.7 | na | 73.9 | 76.1 | 73.4 | 76.7 | 78.0 | |
| % | — | na | 99 | 102 | 98 | 103 | 104 | |
| McKenney SR Niacin | | | | | | | | |
| Drop n | — | 0 | 1 | 2 | 4 | na | 5 | 12 |
| | — | — | — | — | — | — | — | 23 |
| % | — | 0 | 4 | 9 | 17 | na | 22 | 52 |
| Invention Dosage | | | | | | | | |
| Drop n | — | — | 0 | 0 | 0 | 0 | 0 | 0 |
| | — | — | 26 | 67 | 97 | 35 | 15 | 240 |
| % | — | — | 0 | 0 | 0 | 0 | 0 | 0 |
| 1 year | — | — | 15 | 47 | 77 | 31 | 15 | 184 |
| 1 year | — | — | 58 | 69 | 79 | 89 | 100 | 77 |

Dosed twice-per-day as described in "A Comparison of the Efficacy and Toxic Effects of Sustained -vs. Immediate -Release Niacin in Hypercholesterolemic Patients" by McKenney, et al., Journal of the American Medial Association, Mar. 2, 1994; Vol. 271, No. 9, pages 672-677.
[b]SR is "sustained release"
[c]Dosed once-per-day at night The results of the comparison of the studies reported in TABLE VIII show that the control group (the McKenney group) had 12 of 23, or 52 percent of the patients therein drop out of the test because of an increase in their respective liver function tests. The patients withdrew at the direction of the investigator. In comparison, a group of 240 patients treated according to the present invention had zero patients drop out, based upon the same criteria for withdrawal. The test results reported above indicate that this sustained release dosage form caused no elevation in liver function tests (i.e., no liver damage), no elevations in uric acid and only a small, 7.5% increase in fasting glucose levels which in fact decreased during continued therapy.

Thus it should be evident that the compositions and method of the present invention are highly effective in controlling hyperlipidemia in hyperlipidemics, by reducing the levels of LDL cholesterol, triglyceride and Lp(a) while increasing HDL cholesterol levels. The present invention is also demonstrated not to cause elevations, in liver function tests, uric acid or glucose levels for the hyperlipidemics.

Based upon the foregoing disclosure, it should now be apparent that the use of the compositions and methods described herein will carry out the objects set forth hereinabove. It is, therefore, to be understood that any variations in sustained release formulation evident fall within the scope of the claimed invention and thus, the selection of specific component elements can be determined without departing from the spirit of the invention herein disclosed and described. In particular, sustained release excipients, binders and processing aids according to the present invention are not necessarily limited to those exemplified hereinabove. Thus, the scope of the invention shall include all modifications and variations that my fall within the scope of the attached claims.

What is claimed is:

1. A method for treating hyperlipidemia in a hyperlipidemic, the method comprising the step of:
   dosing the hyperlipidemic once a day, in the evening or at night, with at least one sustained release solid oral dosage form comprising (i) about 375 mg of nicotinic acid; (ii) about 5% to about 50% by weight of hydroxypropyl methylcellulose; (iii) about 1% to about 5% by weight of povidone; and (iv) about 0.5% to about 2.0% by weight of stearic acid, wherein the hyperlipidemic's total cholesterol, LDL cholesterol, triglycerides and Lp(a) are reduced and the hyperlipidemic's HDL cholesterol is increased, wherein the total amount of nicotinic acid dosed to a hyperlipidemic in a day is between about 1000 to about 3000 mgs.

2. A method for treating hyperlipidemia in a hyperlipidemic, the method comprising the step of:
   dosing the hyperlipidemic once a day, in the evening or at night, with at least one sustained release solid oral dosage form comprising (i) about 500 mg of nicotinic acid; (ii) about 5% to about 50% by weight of hydroxypropyl methylcellulose; (iii) about 1% to about 5% by weight of povidone; and (iv) about 0.5% to about 2.0% by weight of stearic acid, wherein the hyperlipidemic's total cholesterol, LDL cholesterol, triglycerides and Lp(a) are reduced and the hyperlipidemic's HDL cholesterol is increased, wherein the total amount of nicotinic acid dosed to a hyperlipidemic in a day is between about 1000 to about 3000 mgs.

3. A method for treating hyperlipidemia in a hyperlipidemic, the method comprising the step of:
   dosing the hyperlipidemic once a day, in the evening or at night, with at least one sustained release solid oral dosage form comprising (i) about 750 mg of nicotinic acid; (ii) about 5% to about 50% by weight of hydroxypropyl methylcellulose; (iii) about 1% to about 5% by weight of povidone; and (iv) about 0.5% to about 2.0% by weight of stearic acid, wherein the hyperlipidemic's total cholesterol, LDL cholesterol, triglycerides and Lp(a) are reduced and the hyperlipidemic's HDL cholesterol is increased, wherein the total amount of nicotinic acid dosed to a hyperlipidemic in a day is between about 1000 to about 3000 mgs.

4. A method for treating hyperlipidemia in a hyperlipidemic, the method comprising the step of:
   dosing the hyperlipidemic once a day, in the evening or at night, with at least one sustained release solid oral dosage form comprising (i) about 1000 mg of nicotinic acid; (ii) about 5% to about 50% by weight of hydroxypropyl methylcellulose; (iii) about 1% to about 5% by weight of povidone; and (iv) about 0.5% to about 2.0% by weight of stearic acid, wherein the hyperlipidemic's total cholesterol, LDL cholesterol, triglycerides and Lp(a) are reduced and the hyperlipidemic's HDL cholesterol is increased, wherein the total amount of nicotinic acid dosed to a hyperlipidemic in a day is between about 1000 to about 3000 mgs.

\* \* \* \* \*